(12) United States Patent
Mahfouz

(10) Patent No.: US 8,831,302 B2
(45) Date of Patent: Sep. 9, 2014

(54) IMPLANT DESIGN ANALYSIS SUITE

(76) Inventor: Mohamed Rashwan Mahfouz, Knoxville, TN (US)

( * ) Notice: Subject to any disclaimer, the term of this patent is extended or adjusted under 35 U.S.C. 154(b) by 1181 days.

(21) Appl. No.: 12/673,640

(22) PCT Filed: Aug. 18, 2008

(86) PCT No.: PCT/US2008/009837
§ 371 (c)(1),
(2), (4) Date: Dec. 27, 2010

(87) PCT Pub. No.: WO2009/025783
PCT Pub. Date: Feb. 26, 2009

(65) Prior Publication Data
US 2011/0087465 A1    Apr. 14, 2011

Related U.S. Application Data

(60) Provisional application No. 60/965,195, filed on Aug. 17, 2007.

(51) Int. Cl.
*G06K 9/00*    (2006.01)

(52) U.S. Cl.
USPC ................................ 382/128; 703/6; 703/11

(58) Field of Classification Search
USPC ........................... 382/128; 703/6, 11; 700/117
See application file for complete search history.

(56) References Cited

U.S. PATENT DOCUMENTS

| 6,701,174 B1 * | 3/2004 | Krause et al. ................ 600/407 |
| 7,239,908 B1 | 7/2007 | Alexander et al. |
| 7,269,241 B2 | 9/2007 | Siltanen et al. |
| 7,747,305 B2 * | 6/2010 | Dean et al. ................... 600/407 |
| 7,823,460 B2 * | 11/2010 | White ............................. 73/804 |
| 7,837,621 B2 * | 11/2010 | Krause et al. ................ 600/300 |
| 8,224,632 B2 * | 7/2012 | Whirley et al. ................... 703/7 |
| 2003/0040806 A1 | 2/2003 | MacDonald |
| 2004/0039259 A1 | 2/2004 | Krause et al. |
| 2004/0068187 A1 | 4/2004 | Krause et al. |
| 2004/0102866 A1 * | 5/2004 | Harris et al. ................. 700/117 |
| 2005/0010444 A1 | 1/2005 | Iliff |
| 2006/0094951 A1 * | 5/2006 | Dean et al. ................... 600/407 |
| 2006/0195198 A1 | 8/2006 | James |

(Continued)

FOREIGN PATENT DOCUMENTS

| WO | 2008112996 A1 | 9/2008 |
| WO | PCT/US08/09837 | 1/2009 |
| WO | PCT/US08/09837 | 4/2010 |

OTHER PUBLICATIONS

Dennis et al, Coventry Award Paper, Multicenter Determination of In Vivo Kinematics After Total Knee Arthroplasty, Clinical Orthopaedics and Related Research, No. 416, pp. 37-57, c 2003 Lippincott Williams & Wilkins, Inc., USA.

(Continued)

*Primary Examiner* — John Strege
(74) *Attorney, Agent, or Firm* — Norton Rose Fulbright Canada LLP

(57) ABSTRACT

A method for anatomical analysis and joint implant design. Embodiments provide users with the ability to anatomically analyze a single bone or a series of bones that exist in a database, evaluate surgical landmarks and axes, identify differences among specific characteristics of a given population, and modify existing implants or create new implant designs based on anatomical analyses.

12 Claims, 27 Drawing Sheets

(56) References Cited

U.S. PATENT DOCUMENTS

| | | | |
|---|---|---|---|
| 2007/0081706 | A1 | 4/2007 | Zhou et al. |
| 2007/0118243 | A1* | 5/2007 | Schroeder et al. ............ 700/118 |
| 2007/0168225 | A1 | 7/2007 | Haider et al. |
| 2007/0255288 | A1 | 11/2007 | Mahfouz et al. |
| 2007/0276214 | A1 | 11/2007 | Dachille et al. |
| 2008/0097187 | A1 | 4/2008 | Gielen et al. |
| 2010/0076568 | A1* | 3/2010 | Gupta et al. ............... 623/21.12 |

OTHER PUBLICATIONS

Mahfouz, et al, A Robust Method for Registration of Three-Dimensional Knee Implant Models to Two-Dimensional Fluoroscopy Images, IEEE Transactions on Medical Imaging, vol. 22, No. 12, Dec. 2003, c 2003 IEEE, USA.

Mahfouz et al, Automatic methods for characterization of sexual dimorphism of adult femora: distal femur, Computer Methods in Biomechanics and Biomedical Engineering, 2007, iFirst article, 1-10, c 2007 Taylor & Francis, GB.

Mahfouz et al, Patella sex determination by 3D statistical shape models and nonlinear classifiers, Forensic Science International, FSI-5154, pp. 1-10, c 2007 Elsevier Ireland Ltd., IE.

Merkl et al, Unsupervised Three-Dimensional Segmentation of Medical Images Using an Anatomical Bone Atlas, published in biomedical conference in Singapore, Dec. 2005, University of Tennessee/Department of Mechanical, Aerospace and Biomedical Engrg., Knoxville, TN, USA.

International Search Report and Written Opinion dated Jul. 1, 2010 for PCT/US2010/025466.

International Preliminary Report on Patentability dated Jun. 7, 2011 for PCT/US2010/025466.

International Search Report and Written Opinion dated Apr. 23, 2010 for PCT/US2010/025467.

International Preliminary Report on Patentability dated Oct. 11, 2011 for PCT/US2010/025467.

\* cited by examiner

FIG. 8

IMPLANT DESIGN ANALYSIS SUITE

CROSS REFERENCE TO RELATED APPLICATION

This application claims priority of U.S. Provisional Patent Application No. 60/965,195, filed Aug. 17, 2007, which is hereby incorporated by reference.

PRELUDE

This disclosure is generally related to statistical anatomical shape analysis and modeling of human joints and, more particularly, to a method for transforming statistical analysis into quantitative implant design specifications for existing implants or prototype implants.

Statistical anatomical shape analysis has rapidly established itself as an invaluable tool in the design process for orthopaedic implants. Much research has been performed with the intent of fully describing the anatomy of the long and short bones.

A general approach to measurement strategies of bones has been performed utilizing plain film radiographs, rulers, calipers, goniometers, specialized templates, and osteometric boards. Across these measurement strategies there exists inherent measurement error and user bias, from which arises the need for more precise, three dimensional, and verifiable measurement techniques.

Newer methods have relied on axial plane measurements on CT (computed tomography) image stacks as well as direct segmentation of MRI (magnetic resonance imaging) images for volumetric analysis of articular cartilage and bone. The older methods mentioned above typically provide only rudimentary information regarding linear measurements (resolution in the range of ±1.0 mm) and angular measurements (resolution in the range of ±1.08°). Even when utilizing more accurate measurement techniques such as optical or electromagnetic digitizers or the image-based measurements above, the data is subject to reproducibility errors when human interaction cannot be avoided. While every measurement medium has its inherit bias and imprecision, only a few have attempted to quantify the reliability of their measurements, with a variety of methods being employed. Reliability in measurements is important to avoid statistical type II errors. Unreliable measurements can require larger sample sizes to detect true differences between populations (ethnic, gender, age) or can mitigate correlations between variables.

INTRODUCTION TO THE INVENTION

This disclosure is directed to a method for anatomical analysis and joint implant design. Exemplary embodiments provide users with the ability to anatomically analyze a single bone or a series of bones that exist in a database, evaluate surgical landmarks and axes, identify differences among specific characteristics of a given population, and modify existing implants or create new implant designs based on anatomical analyses, for example.

Embodiments include a method to locate and measure surgically relevant anatomic features and propagate these measurements to different populations using a programmable data processing system, which includes data input means, display means, and data storage means. An exemplary method includes (a) using the data input means to provide the programmable data processing system with the base template bone data set and the match bone data set, the base template bone data set and the match bone data set each including images generated by a biomedical image generation means that may include point-to-point correspondence of surface points across all models in an atlas (e.g., a point on the lesser trochanter of one femur is also on the same part of the lesser trochanter of every other femur model, etc.); (b) storing the base template bone data set and match the bone data set in the data storage means that may include a bone model with average shape characteristics to act as a template mesh; (c) using the programmable data processing system to perform steps in which (1) the centroids of the base template mesh and the new mesh are aligned and the template mesh is pre-scaled to match the bounding box dimensions of the new mesh, (2) a rigid alignment of the template mesh to the new mesh is performed using a vertex-to-vertex iterative closest point algorithm, (3) after rigid alignment, a general affine transformation is performed without iteration, and (4) final surface-to-surface matching creates new points on the surface of the new model, which will have similar local spatial characteristics as the template model; (d) propagating surgically relevant anatomic features and landmarks through an entire population using statistical atlas which establish point correspondence between all the models in the database. In further exemplary form, the points in the template mesh are matched to corresponding points in all other training models, which ensures that all the bones have the same number of vertices and triangular connectivity. Likewise, a smart database may be employed with an independent editor for a user to import, associate, modify and/or query data. In exemplary form, the smart database saves smart bones (three dimensional surfaces, landmarks, axes, and/or measurements, for example) along with their volumetric data, demographics, study related information, and/or contours, for example.

Embodiments may also include a method to transform landmark features and anatomical analysis into quantitative implant design specifications. The method may include analysis and assessments of existing implants or prototype implants. The method may iteratively reassess implants against design and anatomical goals. Exemplary methods quantify surgeons' input by allowing them to perform virtual templating, implant placement, and virtual resection and implant manipulation. Likewise, a feature finder method provides a user with an ability to select a set of bones to analyze and to select what attributes are to be used for data categorization (gender, ethnicity, age, etc., for example). The feature finder method may also allow a user to select which principle components are to be added in the analysis and if the results are to be independent from bone size and/or allow a user to select different color palettes for visualization.

An exemplary feature finder method provides the user with feedback and locations of possible measurements to be conducted to identify these differences. This feature finder method may utilize information from curvature maps, component analysis and/or multiple discriminate analysis, for example. It may also utilize predefined clinical, anthromorphmetric, and/or anatomical measurements and highlights areas on models that would be highly discriminating between given populations (e.g. gender, age, and/or ethnicity, for example). This same method may also provide a user with different curvature mapping (mean, Gaussian, 1/max, etc., for example).

An exemplary feature finder method allows the user to modify or delete suggested measurements and save desired measurements for further analysis. This feature finder method may save all the information in a smart database that keeps track of all these measurements, dependencies and their relationship by means of causal networks or Bayesian belief nets represented in directed acyclic graph DAG structure. The user may modify or delete suggested measurements and the smart database reconfigures dependencies and interdependencies. Likewise, this method may provide the user with ability to select the number of vertices to average during curvature calculation. The method may allow the user to select different color palettes for curvature visualization and may include providing the user with quantitative feedback on bone curvature.

Exemplary modes of variation methods provide the user with the ability to visualize a surface as it varies with each principle component. Modes of variation refers to Component Analysis (sometimes called factor analysis) of both principal and minor components to identify the dependence structure behind a multivariate stochastic observation (statistical atlas) in order to obtain a compact description of it. In exemplary embodiments, the user has the ability to select any combination of principal and minor components and visualize the effect on the bone. The user may also have the ability to input the principal and minor components to supervised and unsupervised neural networks for classification and clustering of a given population or populations.

Exemplary modes of variation methods provide the user with ability to define a region of interest (ROI). The user has the ability to visualize global shape variations or define a region of interest on a bone, for example. The user may then study the variation of the principle and minor components on this local ROI. Further, modes of variation may provide the user with the ability to study surface statistical characteristics (mean and variation, for example) on an entire bone or a defined ROI among a selected bone set. The user may have the ability to apply any statistical analysis on the bone set and predict the effect of noisy or missing data on the shape of bone.

Exemplary modes of variation methods provide the user with ability to generate animation of surface change with each principle using specified step, mean and standard deviation. The modes of variation method (or component analysis method) provides the user with the ability to generate animation of surface changes with each principal or minor component using a specified step (number of frames), mean and standard deviation, for example. Exemplary modes of variation methods provide the user with ability to export generated animations into video files for demonstration.

Exemplary modes of variation methods provide the user with ability to generate synthetic bones based on specified numbers of principal components. The modes of variation methods (or component analysis methods) provides the user with ability to generate synthetic bones based on a specified numbers of principal and minor components.

Exemplary modes of variation methods provide the user with ability to extrapolate missing parts in partial bones based on a selected atlas. The modes of variation method (or component analysis method) provides the user with ability to extrapolate missing parts in partial bones based on component analysis and statistical inference.

An exemplary contouring editor provides the user with ability to slice a bone surface in any arbitrary direction and generate a 3D contour. The user may generate a three dimensional grid by contouring a surface along an arbitrary direction for a user defined number of steps. The user may perform manual measurements on generated contours (such as, for example, distance, angle, etc.). The user may perform automatic measurements including area measurements, moments of inertia, and perimeter measurements, for example, on generated contours. The user may manipulate and/or edit generated contours. The user may export contours to a spreadsheet format, or a text format, for example.

An exemplary joint module includes the following editors: implant editor, virtual resection editor, landmark editor, measurement editor, contour editor and/or script editor. Joint module refers to knee, hip, ankle, lumbar, shoulder, etc. More generally, a joint module that correspond to any articulating surfaces that constitute a joint in the body. Each of the editors may have a two way connection with a smart database for data saving and retrieval. For example, the editors may interface with an implant database that allows the user to add to existing implant families and manufacturers. Also, an implant editor interface may provide the user the ability to expand the implant database by importing CAD models of implants. Further, an implant editor interface may provide the user the ability to view 3D models of implants or 2D implant footprints of implants from different families and manufacturers. In addition, an implant editor interface may provide the user the ability to perform geometrical measurements on implants, and statistically analyze the results. An implant editor interface may also provides the user the ability to attach implant design parameters to implant 3D models and to view and modify implant design parameters. An implant editor interface may also provide the user the ability to export modified design parameters to any CAD software to update the CAD model and/or to import implant CAD models from any CAD software.

An exemplary landmark editor provides a user with the ability to view predefined landmarks, as well as add, delete or modify user-defined landmarks. Further, the landmark editor may provide a user with the ability to view predefine axes as well as add, delete or modify user-defined axes. A landmark editor may allow a user to define an axis between any predefined or user define landmarks. A Landmark editor may allow a user to modify colors and captions associated with user defined landmarks and axes. A Landmark editor allows a user to select and save batches on a bone surface for localizing search area. A Landmark editor may provide a user with the ability to manually define landmarks and may allow a user to run automatic detection of selected landmarks and axes on selected bone sets.

An exemplary measurement editor allows a user to navigate through predefined and/or user defined measurements. Further, the measurement editor may allow the user to delete or modify user-defined measurements. A measurement editor may allow a user to define new geometric measurements, which may include the distance between landmarks, angles between landmarks, curves or axes, radius of curvature of curves, etc., for example. The measurement editor may allow a user to run selected measurements on selected bone sets and may allow a user to perform manual measurements on selected bone sets (distance, angles and curvature, for example). A measurement editor may provide a user with, the ability to visualize resected bones resultant from fitting and resection processes and may allow a user to define and run measurements on resected bones. A measurement editor may allow a user to view output measurements and run statistical analysis including mean, standard deviation, mean difference, power test, and t-test, for example. The generated measurements and statistics may be saved to a smart database. A measurement editor may provide a user with the ability to export generated measurements into text ASCII, or spreadsheet .xls format, for example.

An exemplary contour editor provides a user with the ability to visualize in 3D and 2D predefined and/or user defined contours from different bone sets including resection contours. The user may define new contours using planes, or free form geometrical shapes, for example. The user may run defined contours on selected bone data sets. A contour editor may provide a user with smart tools for manipulation of generated contours. The user may define measurements on contours, including distances, angles, area, moments of inertia, and perimeter measurements, for example. The user may fit predefined geometrical shapes to generated contours. Also, the user may automatically unwrap 3D contours into 2D contours (footprint). The user may visualize footprint contours overlaid with implant footprint contours. A contour editor may provide a user with the ability to automatically optimize implant contours to fit a population of footprint contours. A contour editor may include a set of intelligent tools for manually manipulating implant footprint contour to fit population. The user may save generated contours to a smart database as well as export contours to text ASCII or spreadsheet xls files, for example.

An exemplary statistical engine provides a user the ability to run different powerful statistical analysis on any measurement data. For example, the statistical analysis includes mean, standard deviation, difference, power test, t-test, and histograms.

Virtual resection may provide the user with the ability to perform implant sizing, placement, and/or visualization on selected bone sets. The user may select implant families of interest on which to run the fitting. The user may choose a surgical technique for placing the component from predefined or user defined techniques. Also, the user may define a new surgical technique for placement of both femoral and tibial components based on landmarks and axes. The user may visualize resections, full intact bone, resected bone, and/or an implant placed on resected bone. In an embodiment, the user may be provided with three 2D orthogonal views and one 3D view for more user-friendly visualization and implant manipulation. The user may modify implant size, family and/or manufacturer. The user may view axes and/or landmarks overlaid on bone. The User may receive feedback on component alignment (varus/valgus, internal/external, etc., for example). Virtual resection may provide the user with visual and/or numerical feedback in the form of rotations and translations from the neutral position during manual manipulation of implant placement, for example. The user may save the fitting results to smart database.

An exemplary script editor provides a user with the ability to define landmarks, axes, measurements, contours and/or mathematical and statistical operators. The script editor provides a user with the ability run landmarks detection, axes detection, measurements, and/or contours on selected bone sets. A script editor provides a user with the ability run mathematical or statistical operators on saved or generated measurements. A script editor provides a user with the ability to define geometrical surfaces (vectors, planes, circle, sphere, etc., for example) based on landmarks or axes. A script editor allows a user to utilize saved surface patches as localized search area for landmark detections. A script editor provides a user with the ability to run queries on a smart database.

An exemplary method for defining an origin and insertions of muscles/tendons and ligaments provides a user with the ability to localize origins and insertions of muscles/tendons and ligaments defined in the Landmark Editor. The anatomical origins and insertions of all the major joints may be predefined in the process of creating the statistical atlas. The user also has the ability to add or modify any of these anatomical landmarks.

BRIEF DESCRIPTION OF DRAWINGS

The detailed description refers to the following figures, in which:

FIG. 8 is a screenshot showing an exemplary automatic measurements editor;

DETAILED DESCRIPTION

Figure 1:
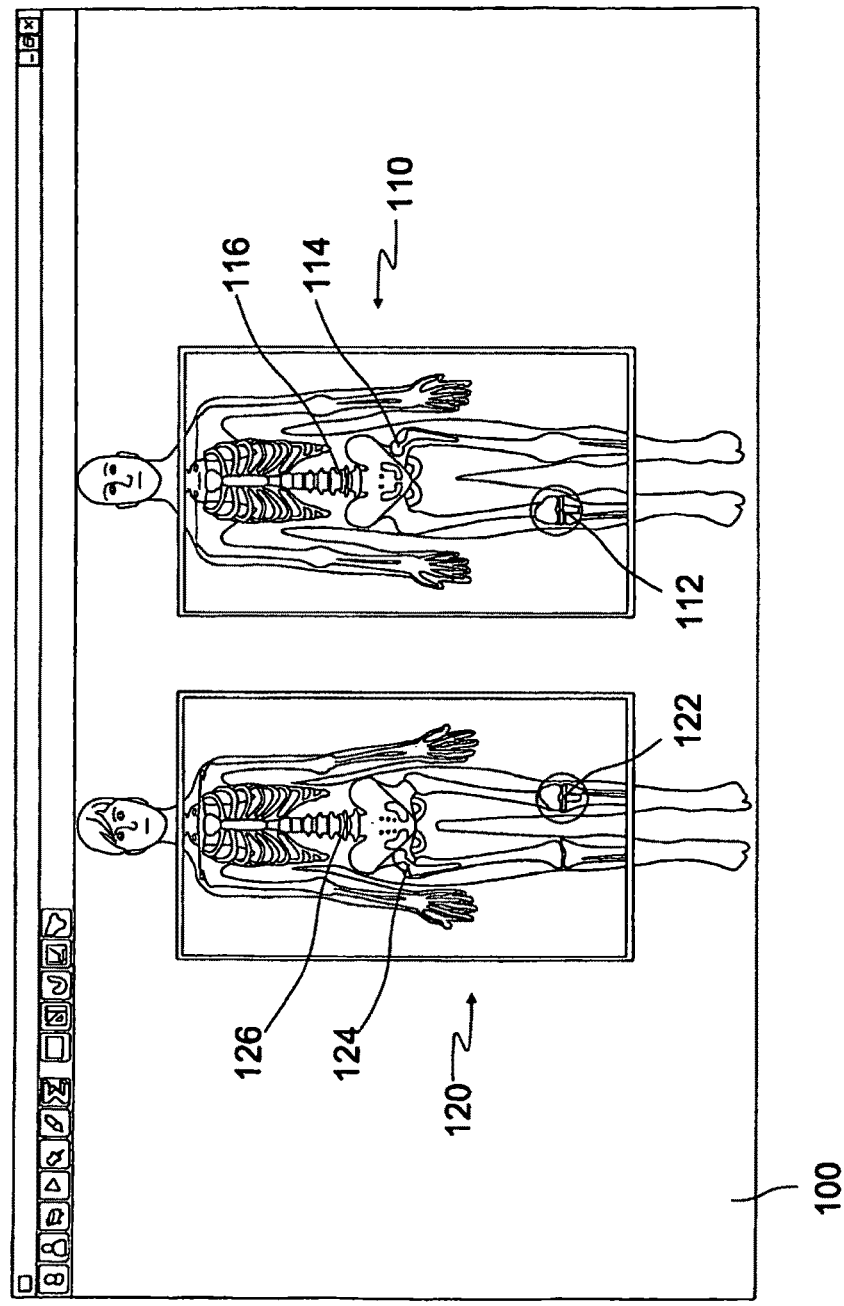
FIG. 1 is a screenshot of and exmplary program main screen.

The exemplary embodiments of the present invention are described and illustrated below to encompass methods generally related to statistical anatomical shape analysis and modeling of human joints and, more particularly, to a method for transforming statistical analysis into quantitative implant design specifications for existing implants or prototype implants. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

To reduce or avoid human reproducibility errors in the design process for orthopaedic implants, an exemplary automatic three dimensional methodology for measuring and identifying bone shape differences in different populations based on statistical atlases may be employed. Matching of surfaces extracted from bone data with a high degree of accuracy may be achieved by creating homologous point sets across similar bones in the dataset, which may be used for the creation of a statistical atlas.

An exemplary statistical atlas may be created by choosing a bone model with average shape characteristics to act as a template mesh. The points in the template mesh may be matched to corresponding points in other training models. This ensures that all of the bones have the same number of vertices and triangular connectivity. Then, a series of registration and warping techniques may be used to select corresponding points on the other bone models in the training set.

In a first step of an exemplary process, the centroids of the template mesh and a new mesh are aligned and the template mesh is pre-scaled to match the bounding box dimensions of the new mesh. Second, a rigid alignment of the template mesh to the new mesh is performed using a standard vertex-to-vertex iterative closest point (ICP) algorithm, for example. Third, after rigid alignment, a general affine transformation without iteration is performed. This method is applied to align the template mesh to the new mesh using 12 degrees of freedom (DOF) (rotations, translations, scaling, and shear).

In an exemplary process, after the affine transformation step, the template and new model may have reached the limits of linear transformation, but local portions of the models may still remain significantly distant. A goal of final surface-to-surface matching is to create new points on the surface of the new model, which will have similar local spatial characteristics as the template model. To reduce this misalignment, point correspondences are picked in both directions (e.g., a point on the lesser trochanter of one femur is also on the same part of the lesser trochanter of every other femur model). For every iteration of the algorithm, the closest vertex-to-vertex correspondences are found from the template to the new model as before, and the correspondences from the new model to the template model are found as well. Using both of these point correspondences, points on the template mesh are moved toward locations on the new mesh using a non-symmetric weighting of the vectors of correspondence:

$$p^{new} = p^{old} + (C_1 W_T - C_2 W_B) \quad (1)$$

where $p^{old}$ represents points on the template model prior to warping, $p^{new}$ represents points after warping, $W_T$ is the correspondence vector that points from the template to the new model, and $W_B$ is the correspondence vector that points from the new model to the template model. $C_1$ and $C_2$ are weighting factors. The vector $W_T$ will have a one-to-one relationship with template points, but the $W_B$ vector initially can have many-to-one or null-to-one relationships with template points.

In an exemplary process, preceding the evaluation of equation (1) in cases of many-to-one relationships, the mean of the many correspondence vectors may be used. The null-to-one relationships create discontinuities in the model surface and thus a smoothing step may be desired. A subroutine consisting of an iterative smoothing algorithm is applied to the now-deformed template mesh. This smoothing algorithm seeks to average the size of adjacent triangles on the template mesh, eliminating discontinuities. At the beginning of the exemplary iterative smoothing algorithm, the algorithm uses the actual areas of the surrounding triangles to dictate the smoothing vector applied to each point. This aids in effectively removing outlying points with large triangles. At the beginning of the process, the template mesh makes large steps and larger smoothing is required. Toward the end of the process, the smoothing vector applied is normalized by the total area of the surrounding triangles, which allows for greater expansion of the template mesh into areas of high curvature. In an exemplary process, after this procedure has been completed on all the bones, principal component analysis (PCA) is performed by first computing the mean femur shape, μ, by averaging the corresponding points across all models. The data matrix is constructed as follows:

$$m_i = ((x_1^i y_1^i z_1^i \Lambda x_N^i y_N^i z_N^i) - \mu)^T \quad (2)$$

$$M = (m_1 | \Lambda | m_B) \quad (3)$$

$$[USV^T] = svd(M) \quad (4)$$

where $m_i$ is the feature vector associated with each B model, the number of points per model is N, the singular value decomposition is represented with svd(M), and the eigenvectors are taken as the leftmost columns of U, given that the singular values along the diagonal of S are sorted from largest to smallest. The eigenvectors, which are orthogonal, define a new set of coordinates with reduced dimensionality with respect to N when the original features $m_i$ are projected onto the eigenvectors scaled by the inverse of the singular values according to:

$$Z_{ij} = \frac{1}{\sigma_j} m_i U_j^T \quad (5)$$

$$1 \le i \le B, 1 \le j \le p$$

where $Z_{ij}$ represents the PCA coordinate for B a model and p represents principal components, with $\sigma_j$ being the singular value associated with column $U_j$ of the eigenvector matrix. The columns of Z are distributed as ~N(0,1), which is the standard normal distribution having a mean of zero and a variance of unity. These PCA coordinates are recorded for each model and are later used in automatic feature generation.

Older measurement techniques utilized in prosthesis design lacked accuracy and/or precision to find anatomical features with the largest significance, while at the same time being unable to find features of smaller consequence. The exemplary embodiments, however, provide advanced interactive and quantitative methods to visualize, extract and measure relevant surgical and anatomical features contained within or across different populations with a high degree of accuracy and repeatability. The exemplary embodiments are also capable of locating and measuring surgically relevant anatomic features and translating these measurements into prosthesis design to greatly facilitate scientific basis for implant design.

The foundation for exemplary applications of this method is based upon the creation of a Smart Database. The Smart Database may include data pertaining to bones (three dimensional surfaces, landmarks, axes, measurements, etc.) along with volumetric data, demographics, study related information, and/or contours, for example. When adding a new model, registration of the case (i.e., bone(s)) must first take place. For example, the user is asked to input the case's demographics which may include information such as the source of the data; whether it be a dry bone, cadaver, or live patient; DICOM (Digital Imaging and Communications in Medicine) data, physician name, hospital location, and additional scan information, for example. Three dimensional NURBS (non-uniform rational b-spline) models may be uploaded to the database which may automatically calculate the placement of various landmarks and axes. All of this data may be stored for later use in the anatomical survey.

Described herein is an exemplary method for an anatomical analysis and prosthesis design. The method may be utilized with one or more joints of the body. FIG. 1 is a screenshot of an exemplary initial screen 100 including a male 110 and a female 120, with those joints 112, 114, 116, 122, 124, 126 available for analysis highlighted. (Other embodiments may permit analysis of different or additional joints; the joints depicted are merely exemplary.) Using this initial screen, as user is allowed to choose which joint 112, 114, 116, 122, 124, 126 to analyze. Notably, an exemplary method allows adding bones from CT or MRI (or any other appropriate imaging technology) to bone and implant repositories. These bones can be dry bones, cadavers, or live patients, for example.

Figure 2:
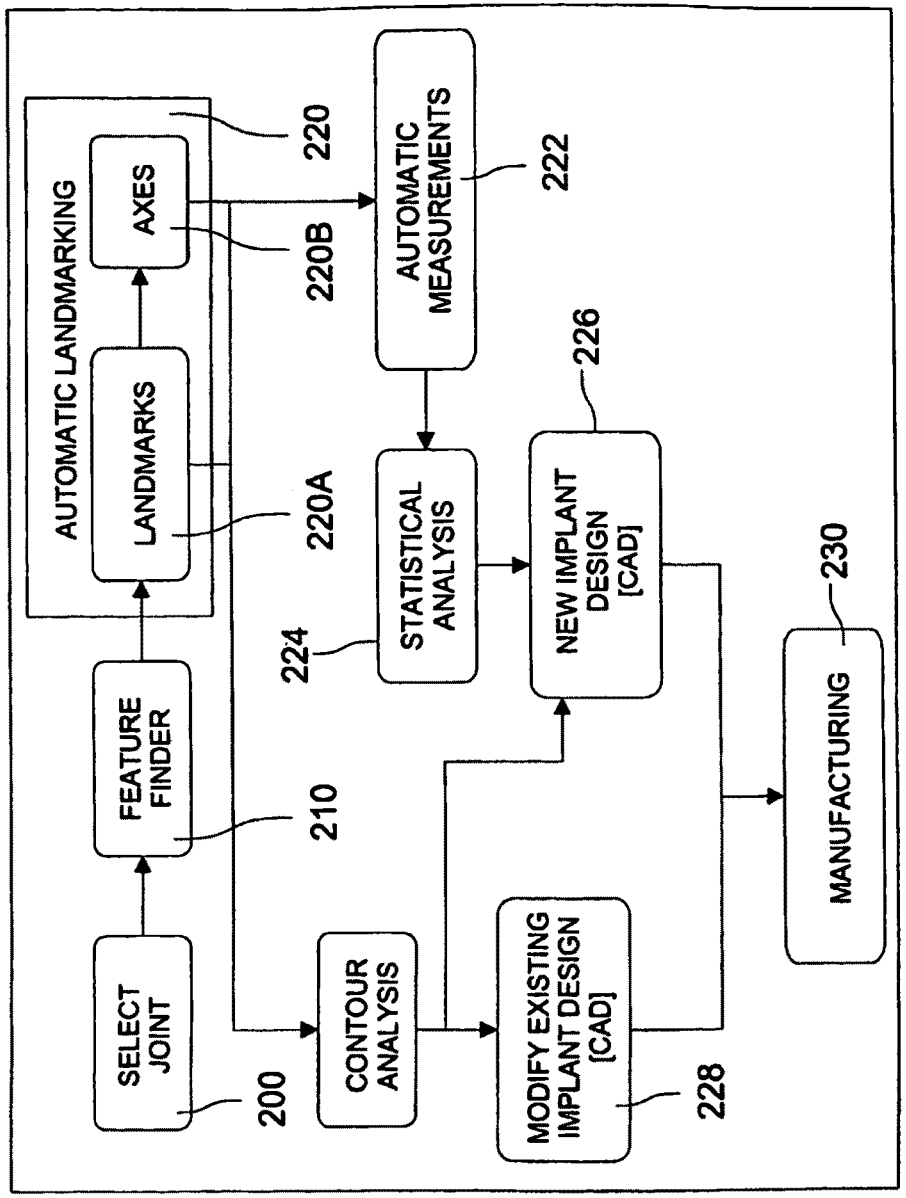
FIG. 2 is a flowchart outlining an exemplary main process for design and modification of existing implants.

FIG. 2 is a flowchart depicting an exemplary process for implant prosthesis design. Upon user selection of the joint of interest 200, such as by using the initial screen 100 to select the joint of interest, the software provides for automatically comparing certain features 210 within this joint across gender, age groups, ethnicities, etc.

Figure 3:
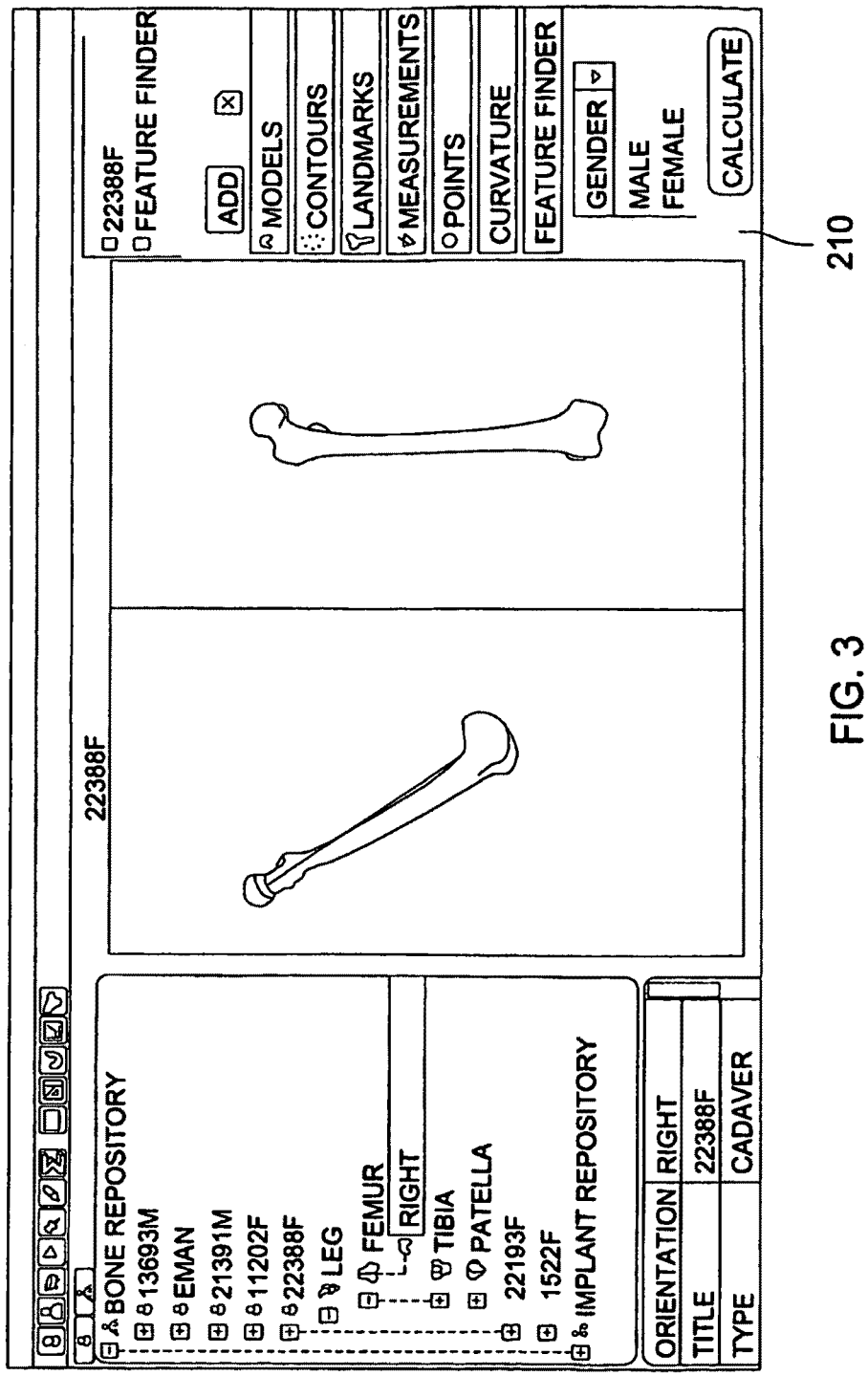
FIG. 3 is a screenshot showing an exemplary feature finder and differences between male and female populations.

FIG. 3 is a screenshot of an exemplary feature finder 210 showing the results for gender as an example. An exemplary feature finder allows a user to select a set of bones to analyze and to select what attributes are to be used for data categorization (e.g., gender, ethnicity, etc.). A feature finder may allow selection of which principle components are to be included in the analysis, selection of whether the results are to be independent of bone size, and selection among different color palettes for visualization of the results, for example. After quantitatively localizing areas of maximum differences between populations, automated landmarking 220 may be performed and the user may be provided the capability to define new landmarks on the bone(s). These landmarks are used to perform measurements 222 (angles or distances) which are then statistically evaluated 224 and used to design new implants 226 or modify existing implants 228. CAD (computer-aided design) models may be generated for the new or modified implants and sent directly to rapid prototype manufacturing equipment 230.

Figure 4:
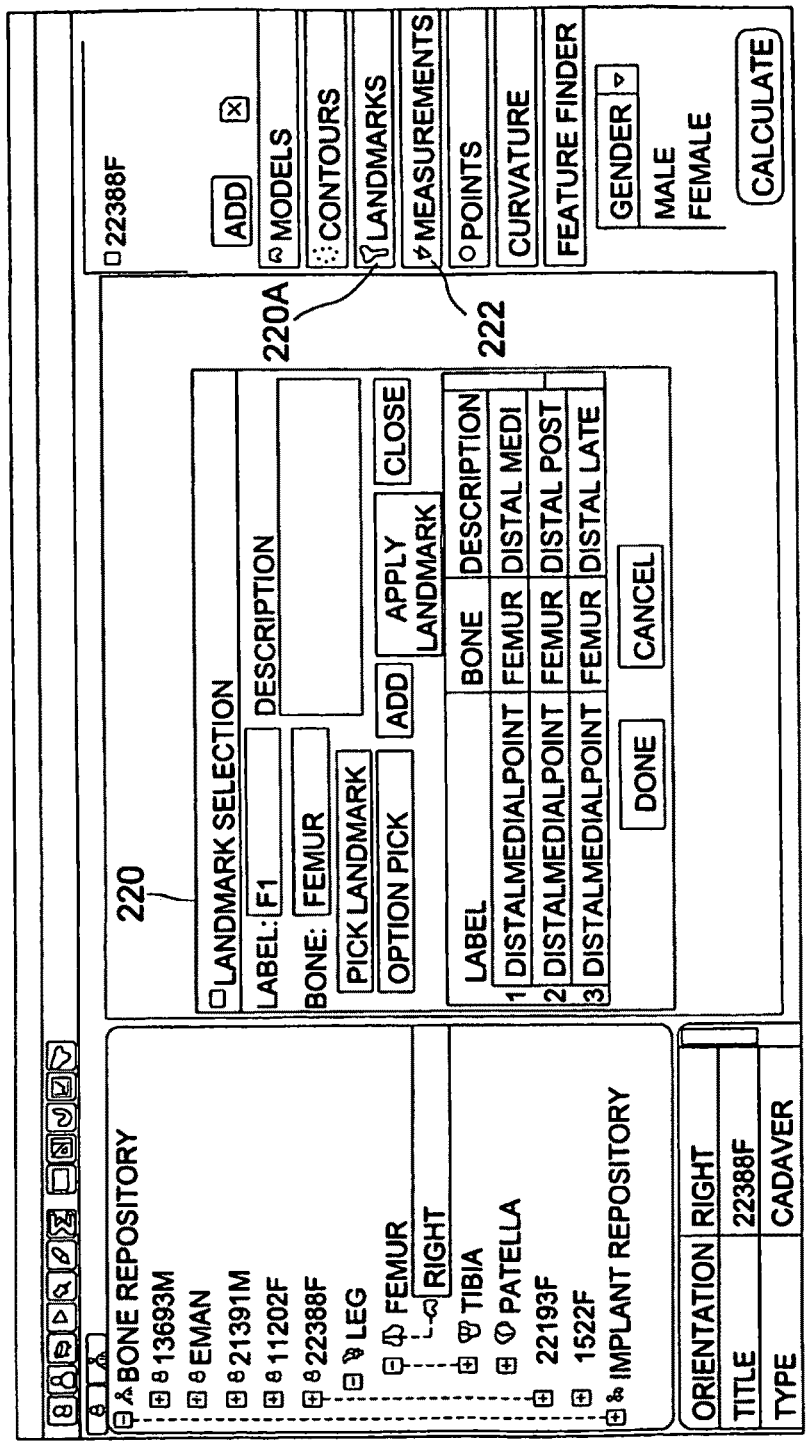
FIG. 4 is a screenshot showing an exemplary automatic landmarking editor.

In an exemplary process, landmarking is performed by more than one method. FIG. 4 is a screenshot showing an exemplary automatic landmarking editor 220. An exemplary system may include predefined landmarks 220A, axes 220B (see FIG. 2), and/or measurements 222, for example.

Figure 5:
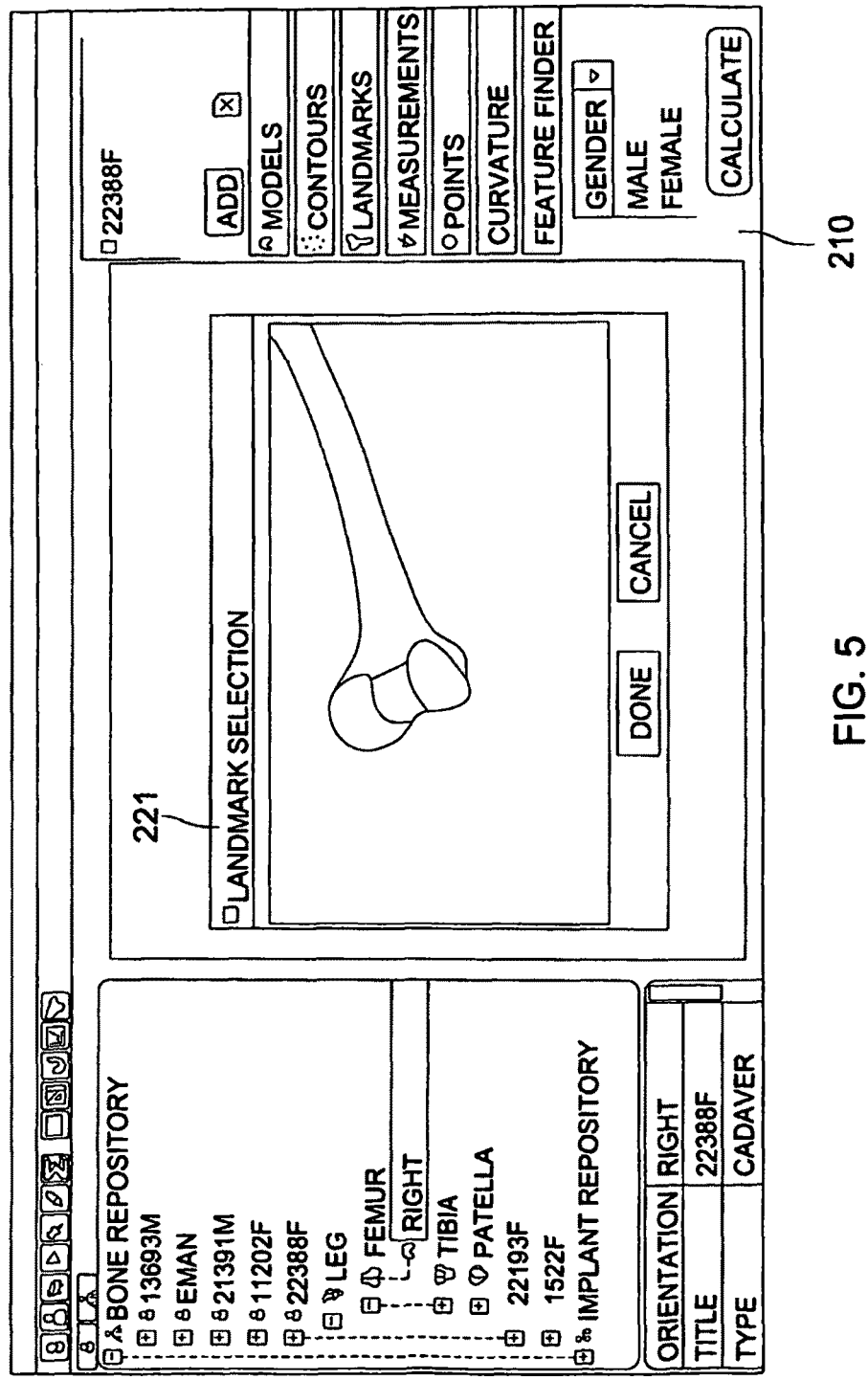
FIG. 5 is a screenshot showing an exemplary direct landmark selection editor.

In an exemplary process, landmarks may also be defined by direct selection of the landmark on a base bone. FIG. 5 is a screenshot showing an exemplary direct landmark selection editor 221. In an exemplary process, the selected landmarks are propagated through a population using a statistical atlas which establishes point correspondence between the models in the database.

Figure 7:
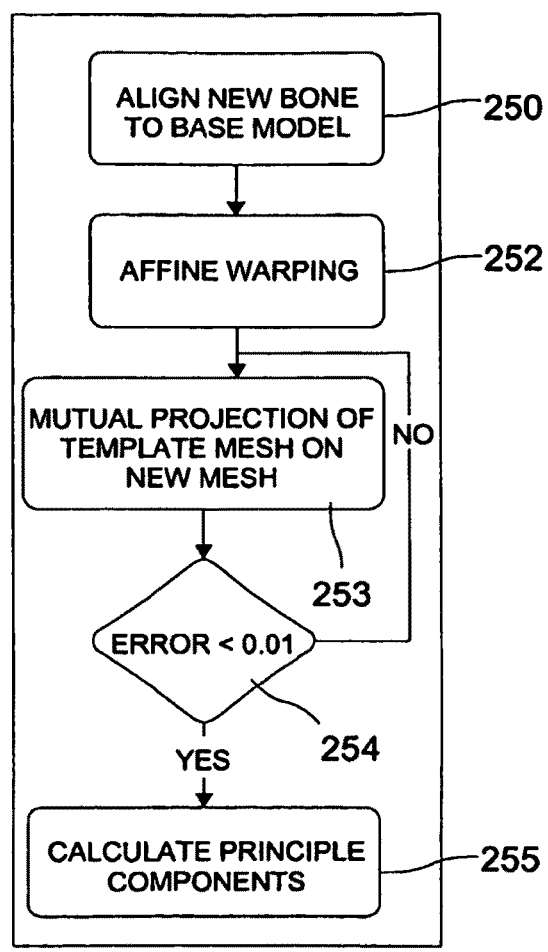
FIG. 7 is a flowchart showing an exemplary method for statistical atlas creation.

FIG. 7 is a flowchart showing an exemplary method for statistical atlas creation. First, in the exemplary method, the centroids of the template mesh and the new mesh are aligned 250 and the template mesh is pre-scaled to match the bounding box dimensions of the new mesh. Second, a rigid alignment of the template mesh to the new mesh is performed using a standard vertex-to-vertex iterative closest point (ICP) algorithm, for example. Third, after rigid alignment, a general affine transformation 252 without iteration is performed. Fourth, the closest point correspondences from the new mesh to the template mesh are calculated and many-to-one relationships are replaced with mean vectors. Closest point correspondences from the template mesh to the new mesh are found and a linear combination of these vectors is used to warp the template mesh, which undergoes an equal element smoothing 253. This process is performed iteratively until the relative error between the template mesh and the new mesh is less than 1% between iterations or no longer changes 254. Principal components analysis is then used to create the statistical atlas from the aligned models 255. This method is applied to align the template mesh to the new mesh using 12 degrees of freedom (DOF) (rotations, translations, scaling, and shear).

In an exemplary method, after the affine transformation step, the template and new model may have reached the limits of linear transformation, but local portions of the models may still remain significantly distant. A goal of final surface-to-surface matching is to create new points on the surface of the new model that have similar local spatial characteristics as the template model. To reduce misalignment, point correspondences are picked in both directions. For every iteration of the algorithm, the closest vertex-to-vertex correspondences are found from the template to the new model as before, and the correspondences from the new model to the template model are found as well. Using both of these point correspondences, points on the template mesh are moved toward locations on the new mesh using a non-symmetric weighting of the vectors of correspondence.

Figure 12:
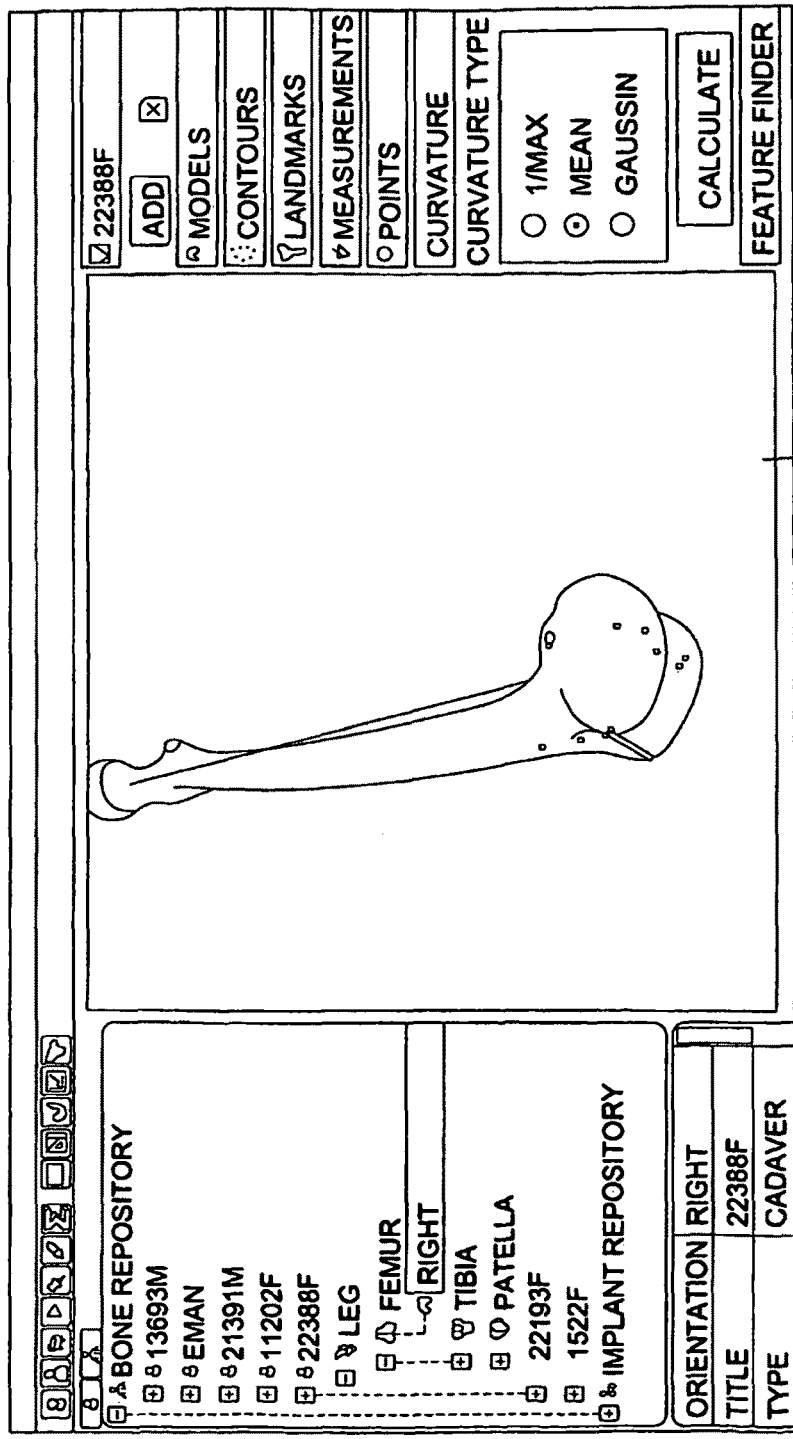
FIG. 12 is a screenshot showing exemplary curvature mapping for femora.

Exemplary embodiments provide curvature mapping as another valuable tool through anatomical surveying. Color maps of the bone's curvature show the convexity or concavity of the bone and present quantitative results using Gaussian, mean, or 1/max, for example. FIG. 12 is a screenshot showing exemplary curvature mapping 280 for femora. In exemplary embodiments, the user may have the ability to select the number of vertices to average during the curvature calculation and/or the ability to select from different color palettes for curvature visualization.

Figure 9:
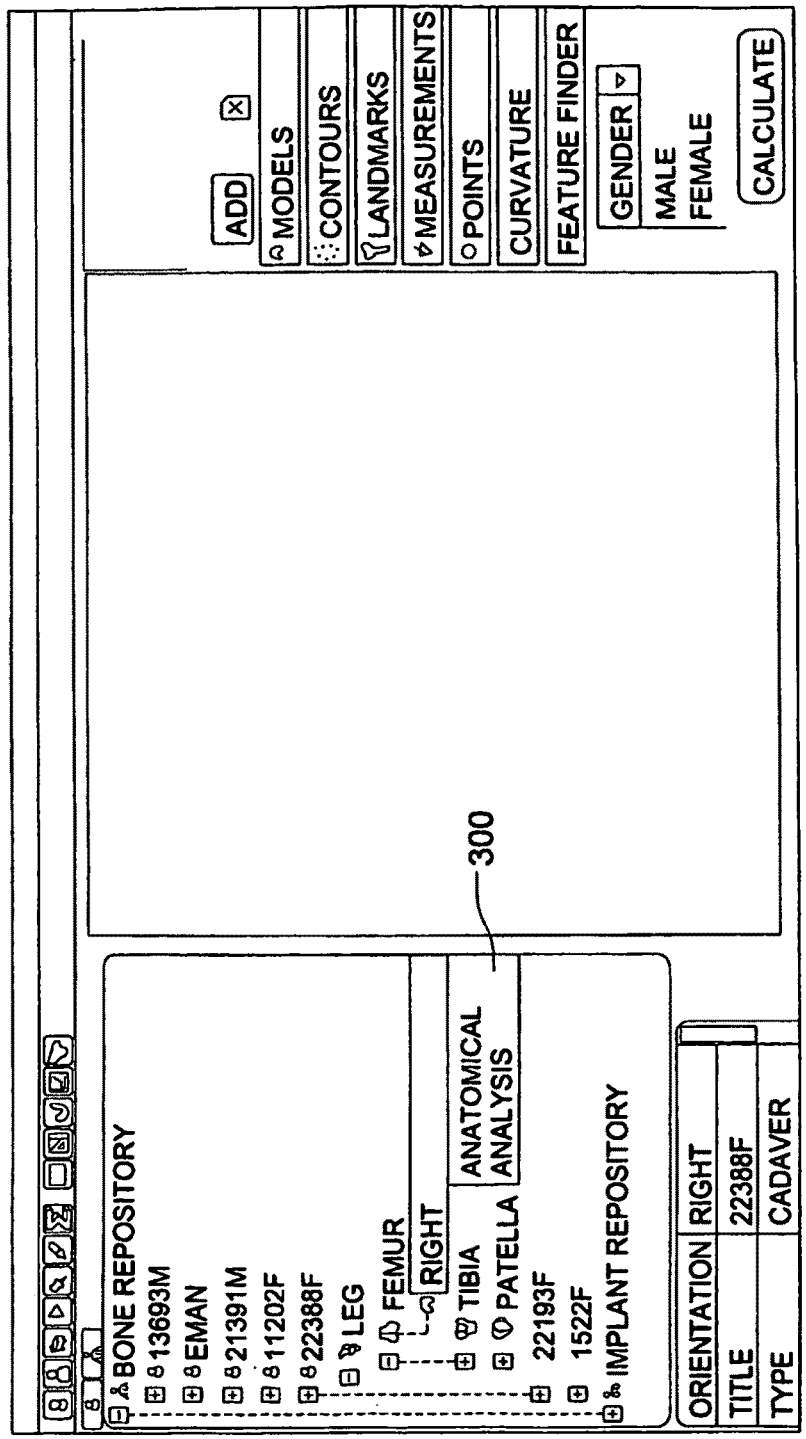
FIG. 9 is a screenshot showing an exemplary project navigator tree.
Figure 10:
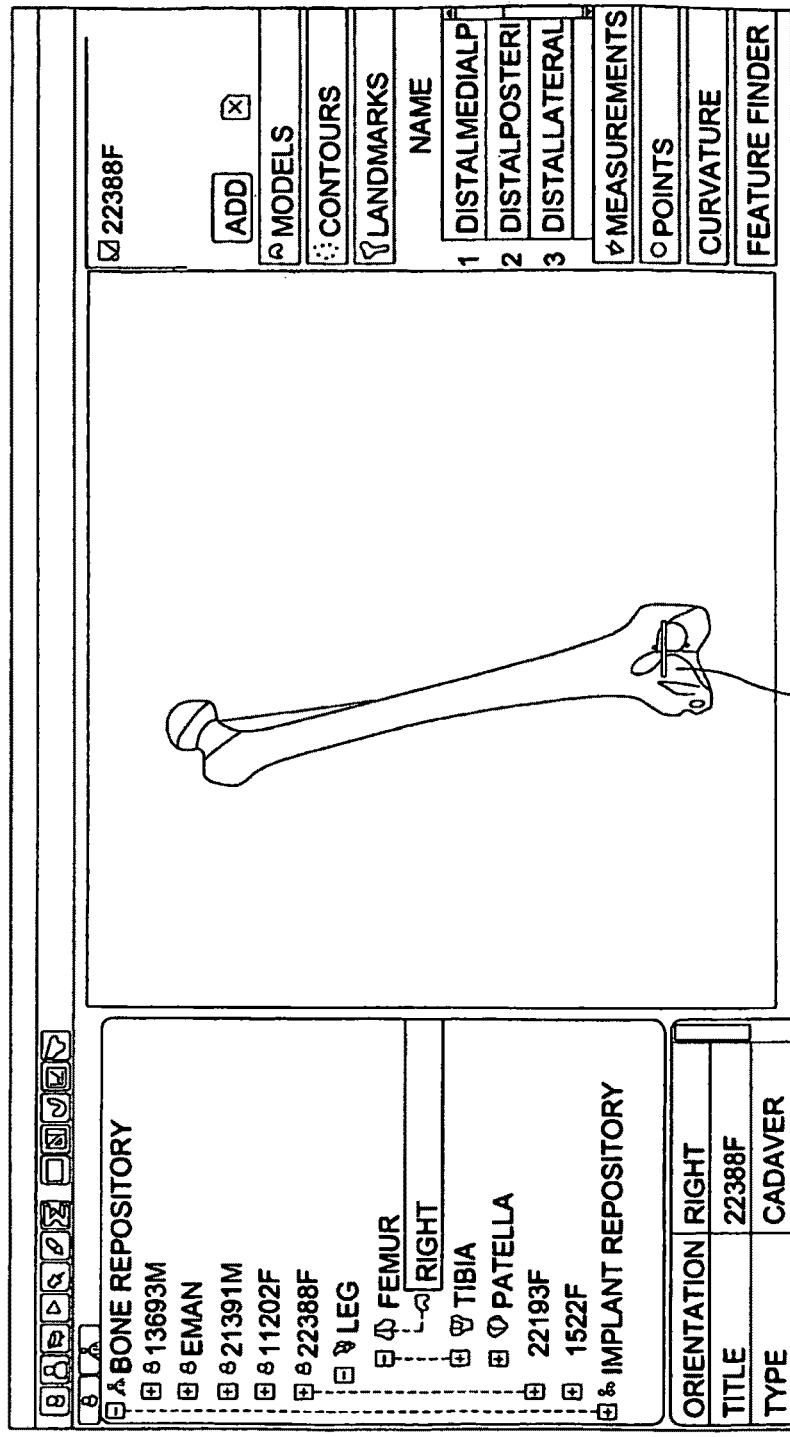
FIG. 10 is a screenshot showing exemplary automatic and user defined landmarks on femora.

An exemplary Anatomical Analysis segment 300 (see FIGS. 9 and 10) allows the user to examine detailed features of a given bone 310. A predefined set of landmarks and axes are automatically generated once a new bone has been added to the Smart Database. If, however, the user wishes to define a new landmark or axis, he may do so by using the Landmark Editor 220. An exemplary Landmark Editor allows a user to view predefined landmarks as well as add, delete, and/or modify user-defined landmarks, for example. In addition, it may allow viewing of predefined axes as well as adding, deleting, and/or modifying user-defined axes. Exemplary Landmark Editors permit users to modify the colors and captions associated with user-defined landmarks and axes. In addition, exemplary Landmark Editors may permit selecting and saving batches of landmarks on bone surfaces for localizing a search area.

Figure 6:
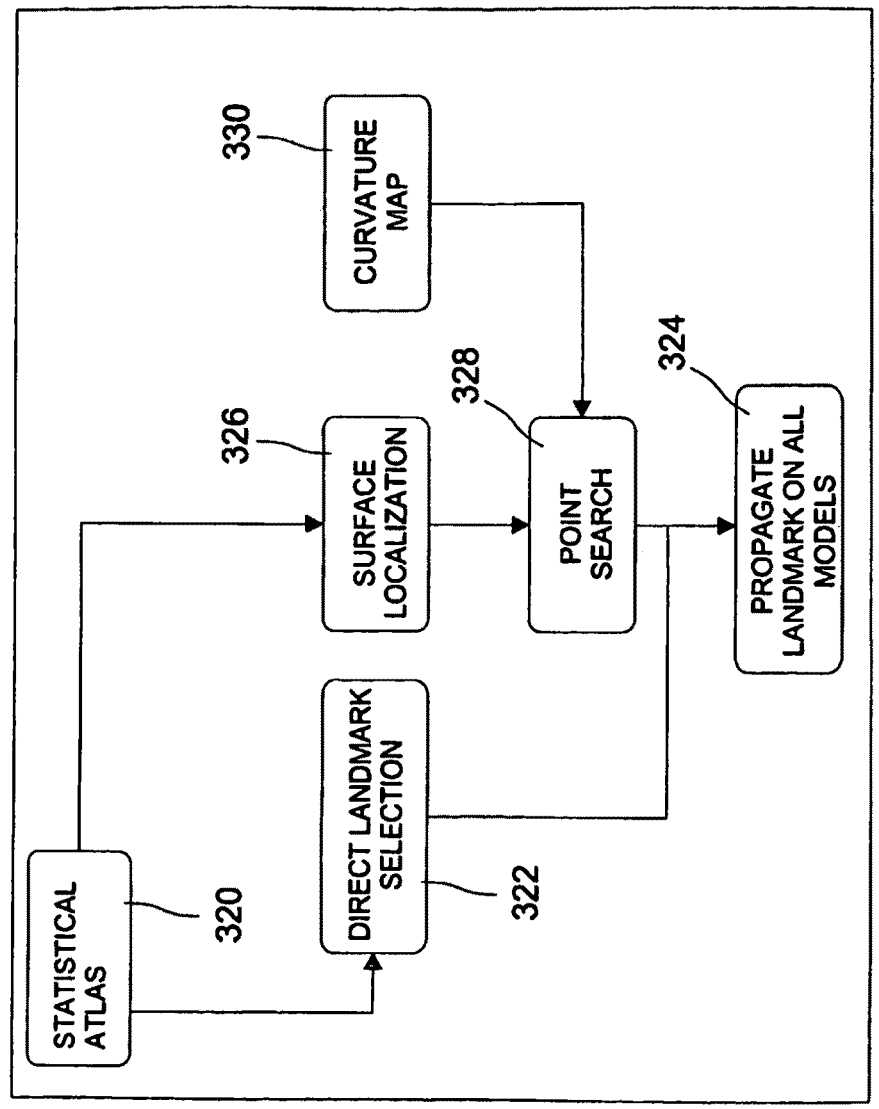
FIG. 6 is a flowchart describing different exemplary landmarking methods.
Figure 13:
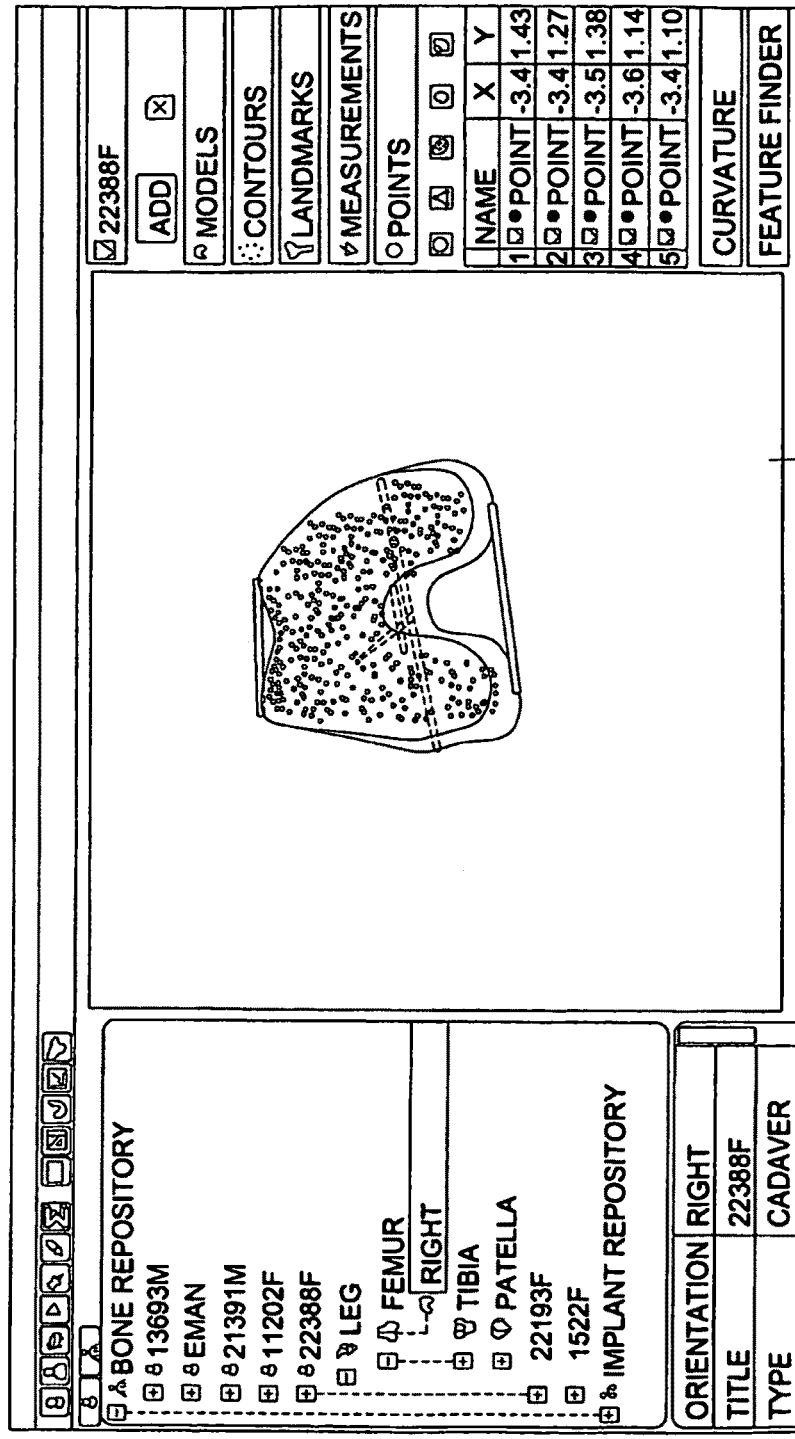
FIG. 13 is a screenshot showing exemplary sub-surface localization.

One way to define a new landmark is through point correspondence. In an exemplary embodiment, the user selects the location on a bone where he/she believes the landmark should exist. If defining a new axis, two already defined landmarks can be chosen or first created and then selected. A second method used to define new points is localizing patches of points on the surface of the bone. FIG. 13 is a screenshot showing exemplary sub-surface localization 290. Different localized search criteria may be applied including curvature values, maximizing or minimizing distance in a certain direction, for example. FIG. 6 is a flowchart describing different exemplary landmarking methods. FIG. 6 evidences the anatomical analysis process 300 (see FIG. 9) performed on an exemplary bone 310 (see FIG. 10) that allows the user to examine detailed features of a given bone 310 or bone model. The statistical atlas block 320 is explained with reference to FIG. 7. The process of creating the statistical atlas results in predefined clinical landmarks, clinical axes, and clinical and anthropological measurements. In addition to the predefined clinical and anthropological landmarks, the user can define a new landmark by direct selection of points on any bone/bone model. An exemplary implementation of direct landmark selection 322 is shown FIGS. 4 and 5. These landmarks are then propagated through entire population 324 using the statistical atlas which establishes point correspondence between all the models in the database. In an exemplary implementation of surface localization 326, the user has the ability to map any area on the surface of a bone by localizing patches of points or a selection of a single point on that surface as shown in FIG. 13. The user may also use a point search 328 to apply localized search criteria on single point or patches of points selected on a surface like maximizing or minimizing distance in a certain direction. The single point or patches of a point search criteria can be applied in conjunction with the curvature map 330 of the bone, an example of which is shown in FIG. 12. The curvature map preserves the surface spatial characteristics that are inherent in the definition of that specific bone. Thus, surface principal curvatures and their directions may be obtained using the screen depicted in FIG. 12. Using the curvature computed at each vertex, combined with a specific single point or patches of points the user can define a point termed the anteriorposterior AP point. For example, in the femur bone, this point is defined as the most proximal portion of the distal anterior intercondylar groove with negative curvature. In essence, it measures the proximal limit of the intercondylar groove. The minimum distance between the AP sizing point and the posterior plane is recorded as AP Size; this new landmark can then be saved for this specific bone or propagated throughout the rest of the statistical atlas database. New landmarks or axes can be saved and propagated throughout the rest of the database or utilized on a single bone, for example.

Figure 8:
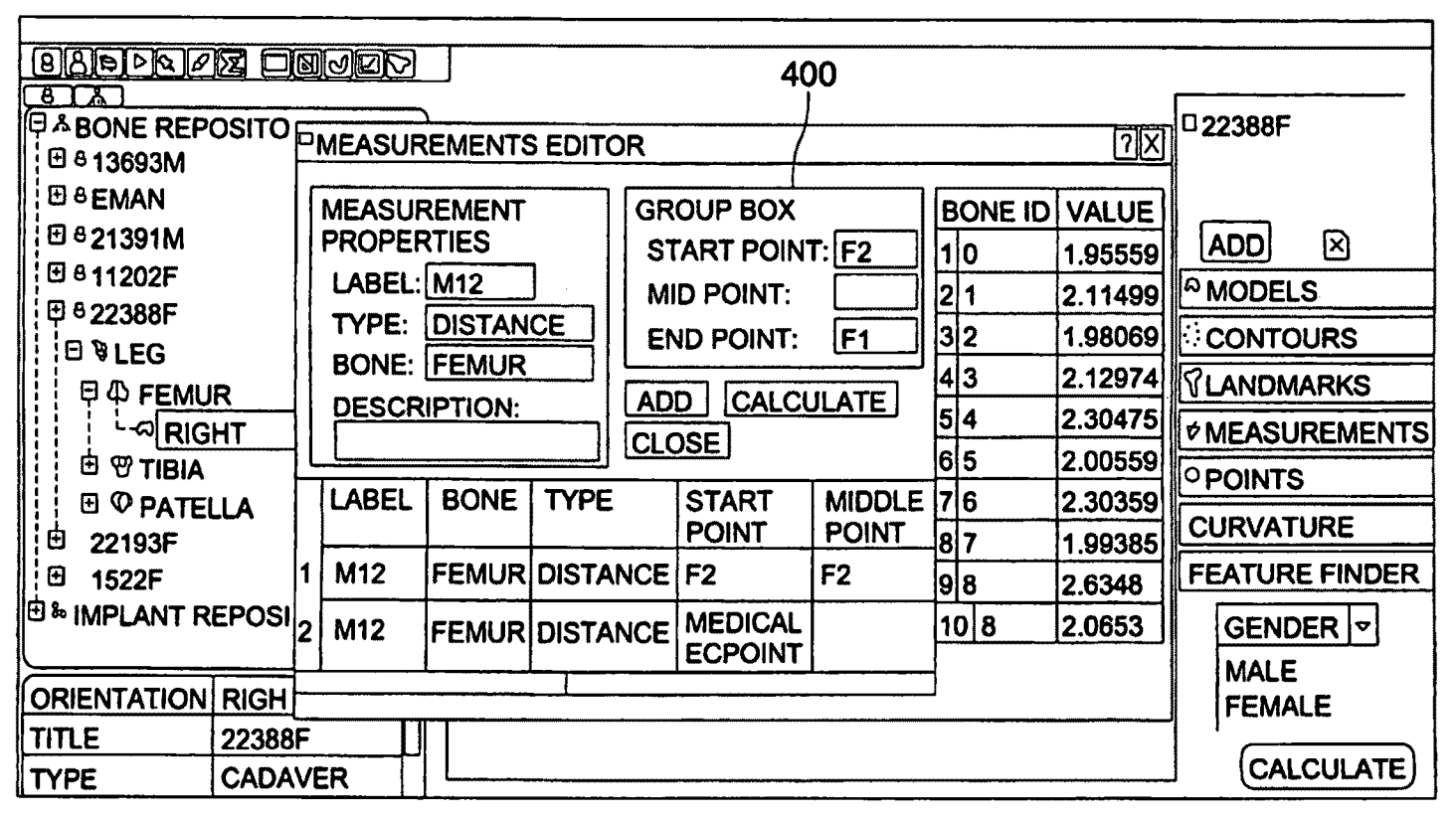

In the exemplary embodiments, just as landmarks and axes can be automatically or manually determined, distance and angular measurements may be determined. An exemplary Measurement Editor allows a user to navigate through predefined and user-defined measurements, as well as add, delete, and/or modify user-defined measurements. For example, selecting two landmarks may calculate the distance between them, while selecting three may provide an angular measurement. Other exemplary geometric measurements include curves or axes, radii of curvature, area moment of inertia, perimeter measurement, etc. FIG. 8 is a screenshot showing an exemplary automatic measurements editor 400. Once again, the user may be given the option to complete these measurements on the remaining data and users may select certain bone sets on which the measurements should be conducted.

Figure 11:
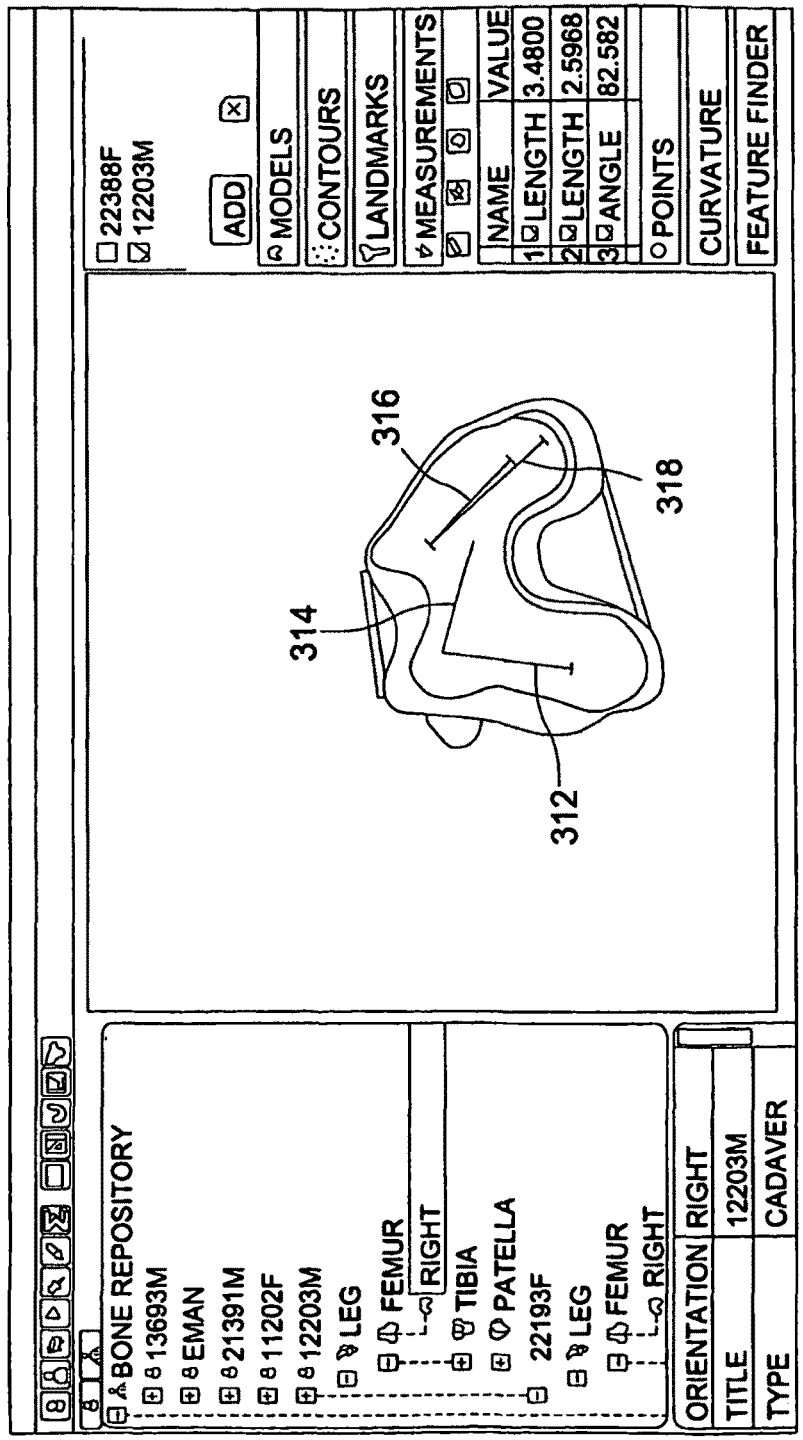
FIG. 11 is a screenshot showing exemplary user defined measurements.

In addition to measurements of intact bones, measurements may be performed on resected bones produced by the resection and fitting process. Statistical analysis can be performed including mean, standard deviation, power test, t-test, mean difference, histograms, and fuzzy c-means and k-means cluster analysis, for example. Generated measurements and statistics may be saved in the smart database or exported in text (such as ASCII) or spreadsheet format (such as .xls), for example. In an exemplary embodiment, automatic measurements may be applied to an entire database; however, manual calculations may only take place on one bone at a time. FIG. 11 is a screenshot showing exemplary user defined measurements 312, 314, 316, 318.

An exemplary Contour Editor studies exact contours in certain areas of the bone. For example, two types of contours may be generated: rotational and translational. In both cases, an axis is defined. However, the plane rotates around the axis along a specified angle measurement in rotational while the planes are cut normal to the axis in translational. Exemplary Contour Editors provide the user with the ability to slice bone surface in any arbitrary direct and generate a corresponding 3D contour, for example. Exemplary Contour Editors provide the user with the ability to generate a three dimensional grid by contouring a surface along an arbitrary direction for a user-defined number of steps. Once the contours have been generated, additional analysis may be performed, such as distance, angle, area, curvature, perimeter, and moment of inertia, one or more of which may be performed automatically. Generated contours may be exported to NURBS standard format (e.g., IGES, STEP, etc.), or to a spreadsheet (e.g., .xls) or text format (e.g., ASCII), for example, and may be saved to the smart database. Exemplary embodiments may provide the user with the capability to manipulate and edit generated contours.

Exemplary Contour Editors may provide the user with the ability to generate and visualize 3D and 2D predefined or user defined contours from different bone sets including resection contours. New contours may be defined using planes or free form geometrical shapes, for example. Users may run defined contours on selected bone datasets. Exemplary Contour Editors may include smart tools which allow users to manipulate generated contours. Users may be able to fit predefined geometrical shapes to generated contours. 3D contours may be automatically unwrapped into 2D contours, which may be referred to as a footprint.

Exemplary Contour Editors allow visualization of footprint contours overlaid with footprint contours of implants and provide the ability to automatically optimize implant contours to fit population footprint contours. Users are also provided with a set of intelligent tools for manually manipulating implant footprint contours to fit populations.

In the exemplary embodiments, throughout the various sections of the Anatomical Survey, measurements may be made and may be used in the Implant Design module. Many of these implant parameters can also be exported to CAD software, such as Unigraphics.

Figure 20A:
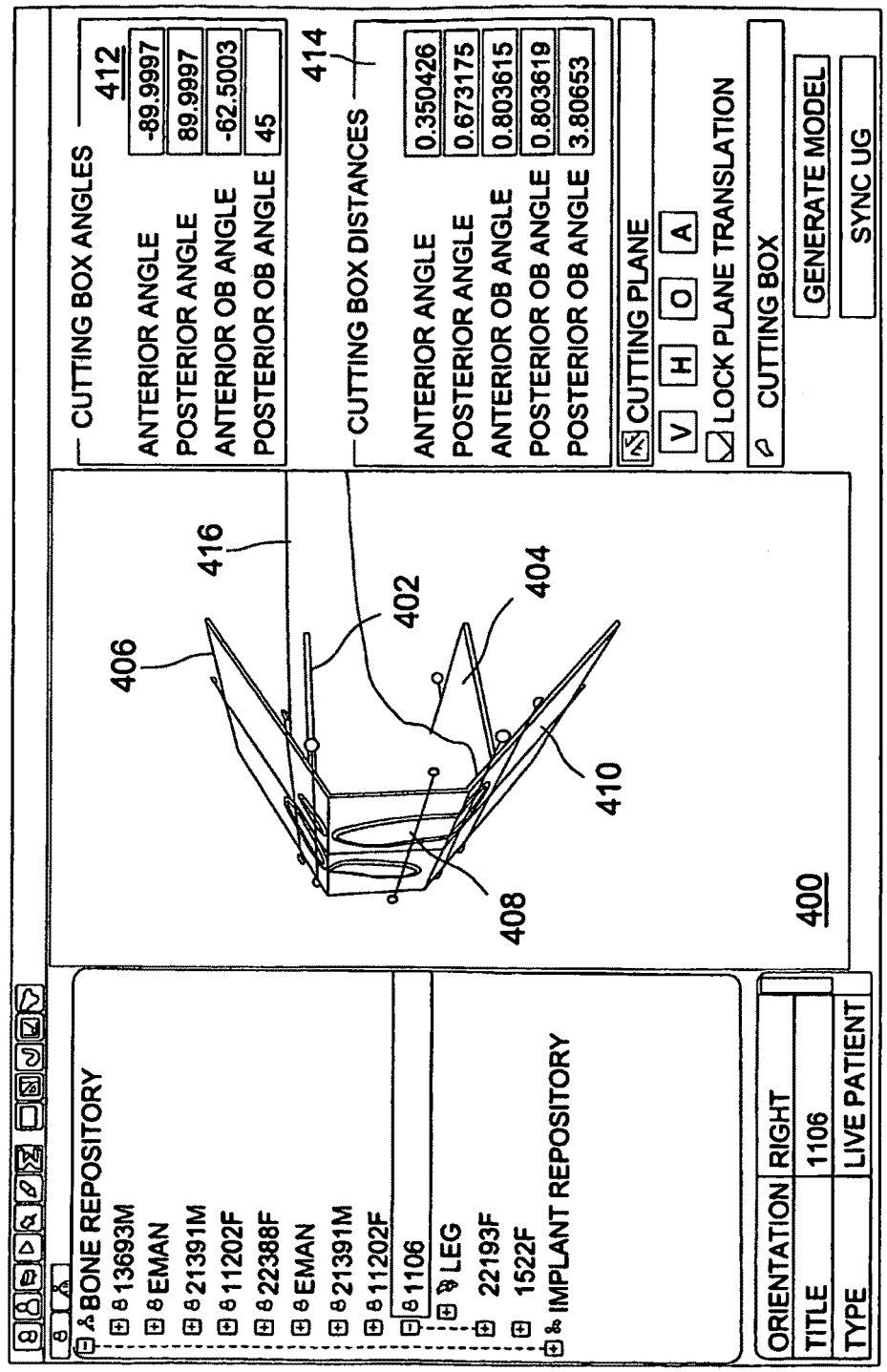
FIG. 20A is a screenshot showing an exemplary cutting box design editor.
Figure 20B:
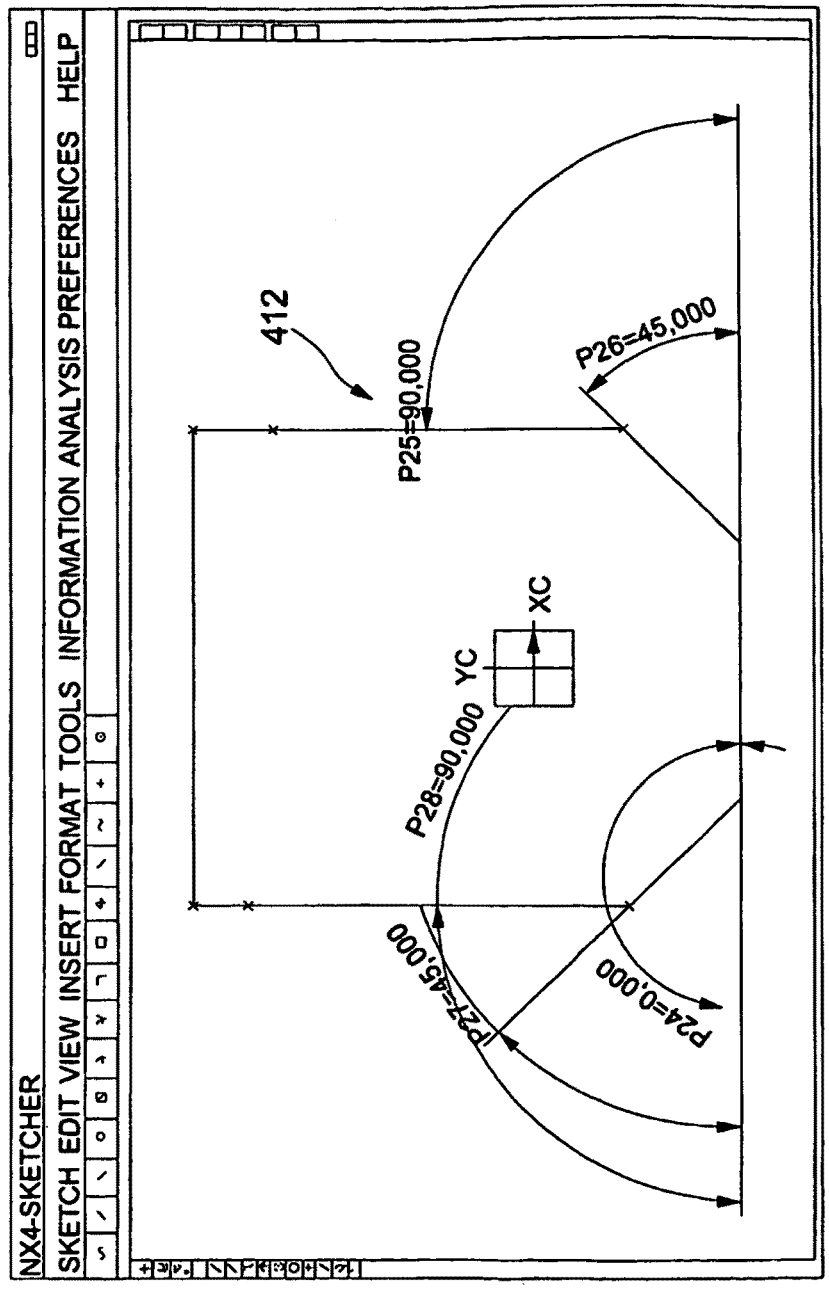
FIG. 20B is a screenshot of exemplary CAD model design parameters in a CAD program.

In an exemplary embodiment, a goal of the Implant Design module is to create new, or modify existing, implants based on a given population. A first step in any joint implant design is typically to determine the cutting planes as shown in FIG. 20. For example, in an exemplary knee Implant Design module, the cutting box is defined by five planes 402, 404, 406, 408, 410 which can be manipulated to create a custom box. The user has the ability to change angles 412 or distances 414 between planes or manually reposition the planes in any direction. FIG. 20 is a screenshot showing an exemplary cutting box design editor 400.

Figure 21:
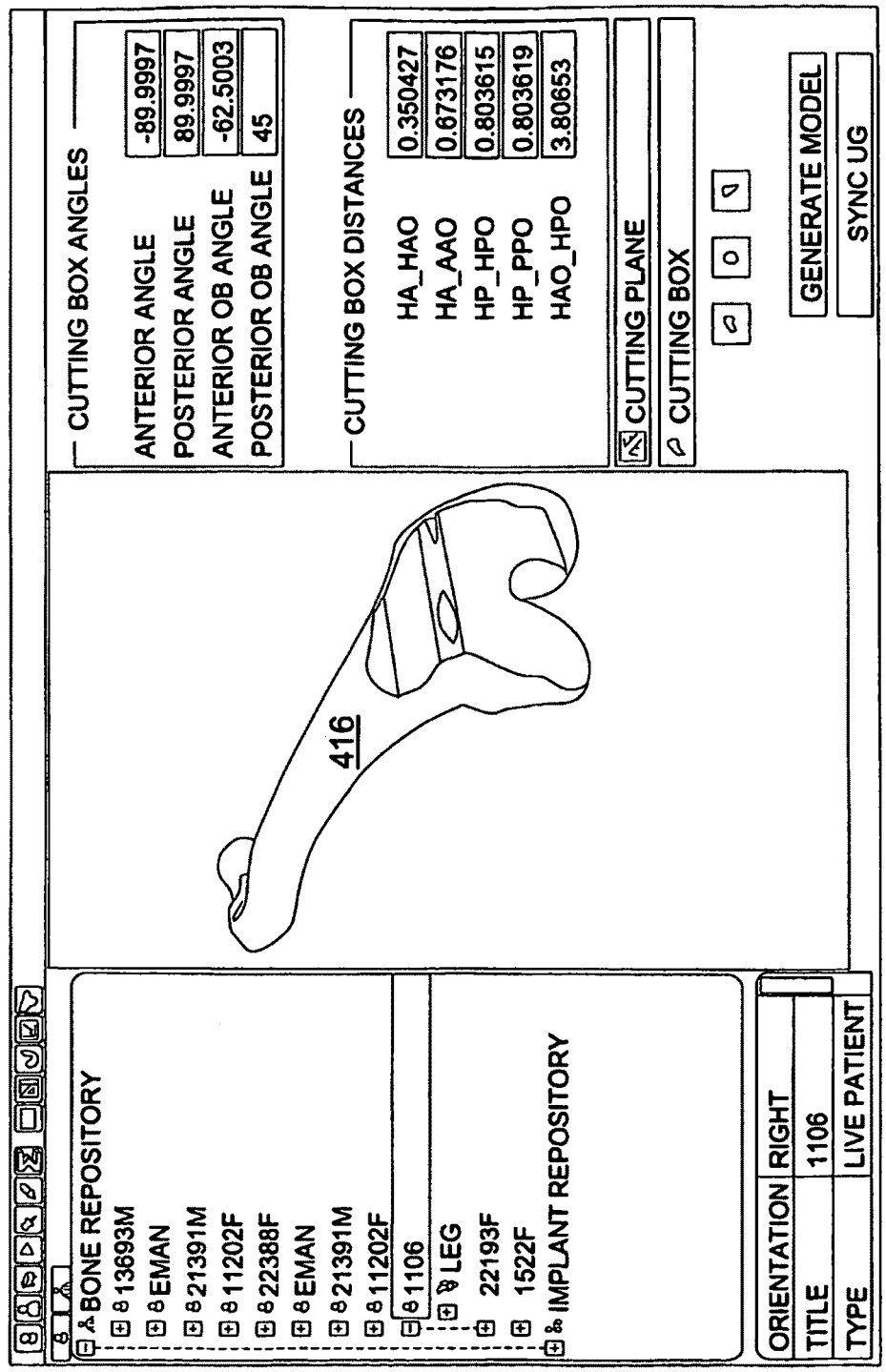
FIG. 21 is a screenshot showing an exemplary generation of a cutting box model and its fitting to a femoral bone.

In an exemplary embodiment, once the planes are in the desired locations, a surface model for the cutting block is generated and the data can be synchronized with CAD software (such as Unigraphics) to generate the cutting box. FIG. 21 is a screenshot showing an exemplary generation of a cutting box model and its fitting to a femoral bone 416. Detailed criteria can also be set if there are certain standards that need to be maintained while designing the cutting box. The five planes may be optimized while taking into account the user defined guidelines.

Figure 22:
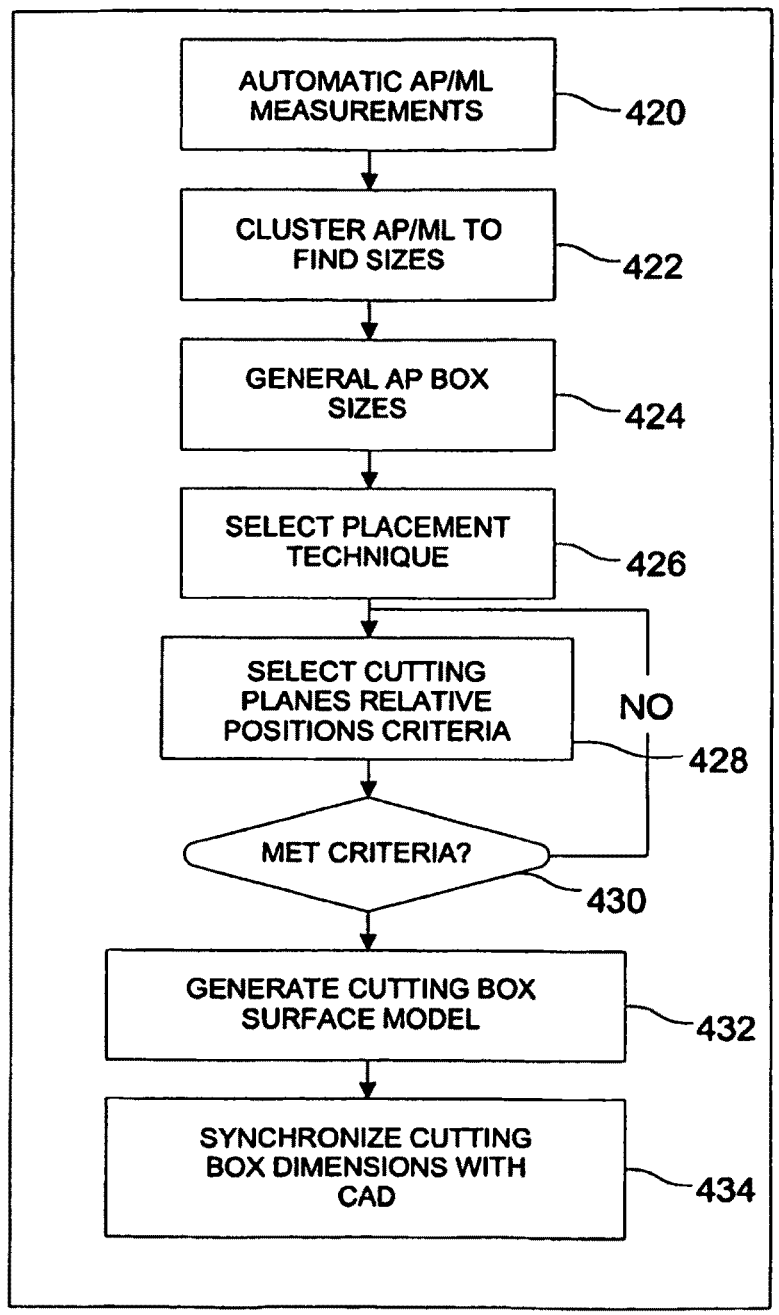
FIG. 22 is a flowchart describing an exemplary process of implant cutting box design automation.

FIG. 22 depicts an exemplary process for designing a cutting box. The process starts by automatically measuring 420 the anterior posterior height and the medial lateral width of the femur across the population as described and shown in FIG. 6. These two measurements are then clustered 422 into a different population using fuzzy C-means to generate AP box sizes 424 across the population. After finding the AP clusters, the next step in the process is to optimize the relative positions of the five cutting planes. This includes the distances and angles between these planes as in FIGS. 9 and 11. The user first defines the surgical criteria 426 for placing the femoral component relative to Posterior condylar axis or Transepicondylar axis. The user then has the ability to define the criteria 428 for finding the optimum relative positions between the cutting planes. An optimization is performed to find the optimum planes to met the user criteria 430. These planes are then used to generate a solid surface model for the cutting box 432. The box design parameters are then transferred to CAD packages 434 for the manufacturing process.

Figure 14:
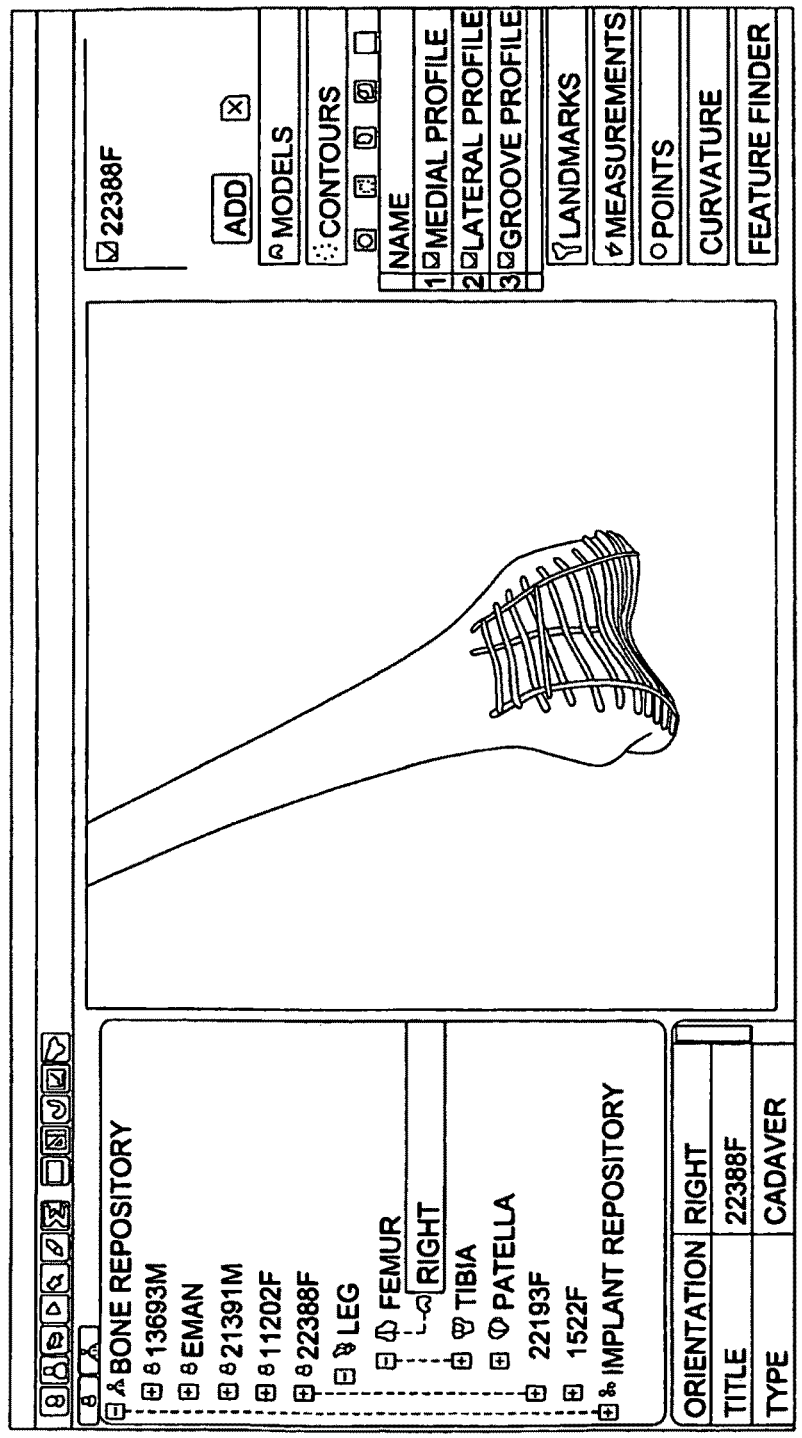
FIG. 14 is a screenshot showing exemplary articular surface mapping.
Figure 15:
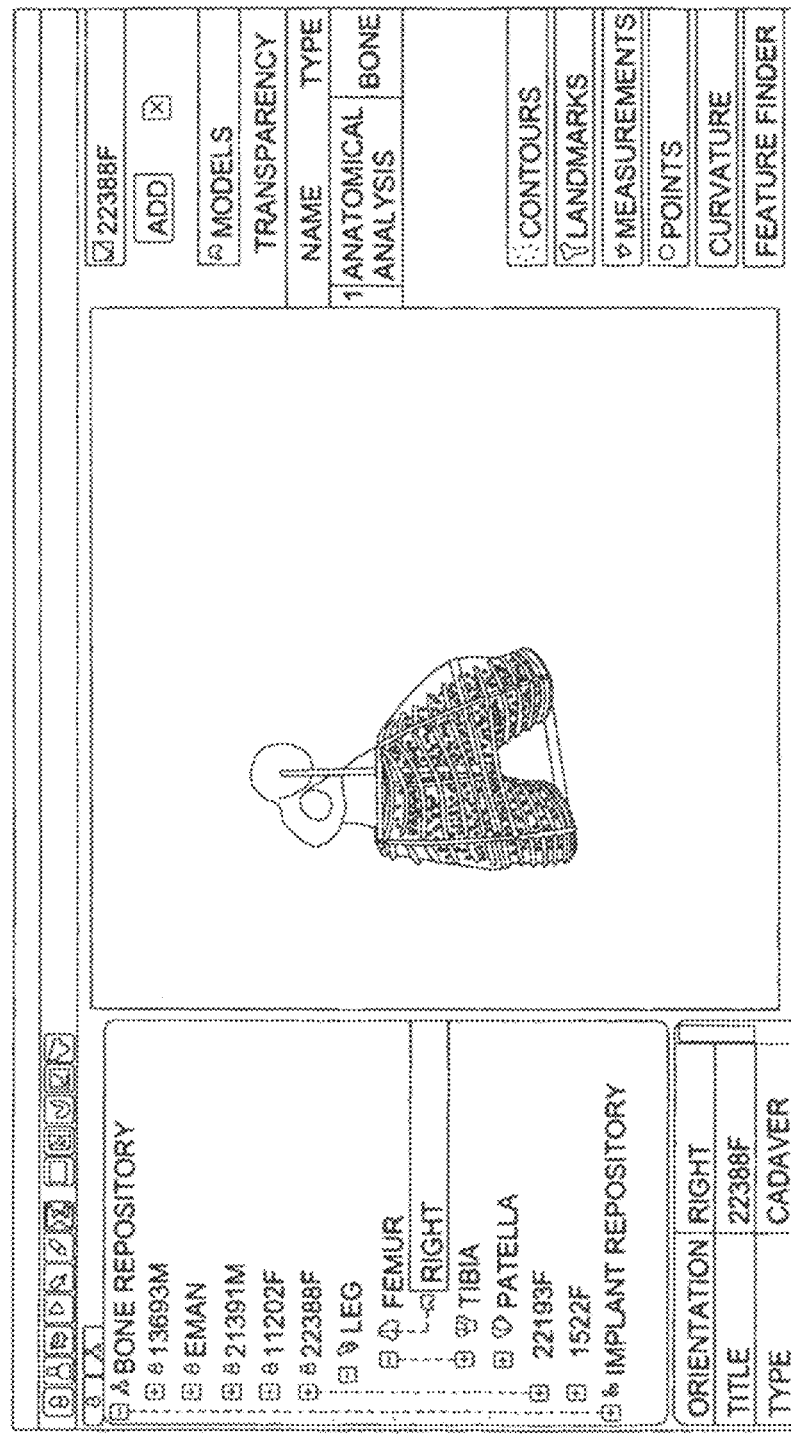
FIG. 15 is a screenshot showing an exemplary translation of an articulate surface into an implant design.
Figure 16:
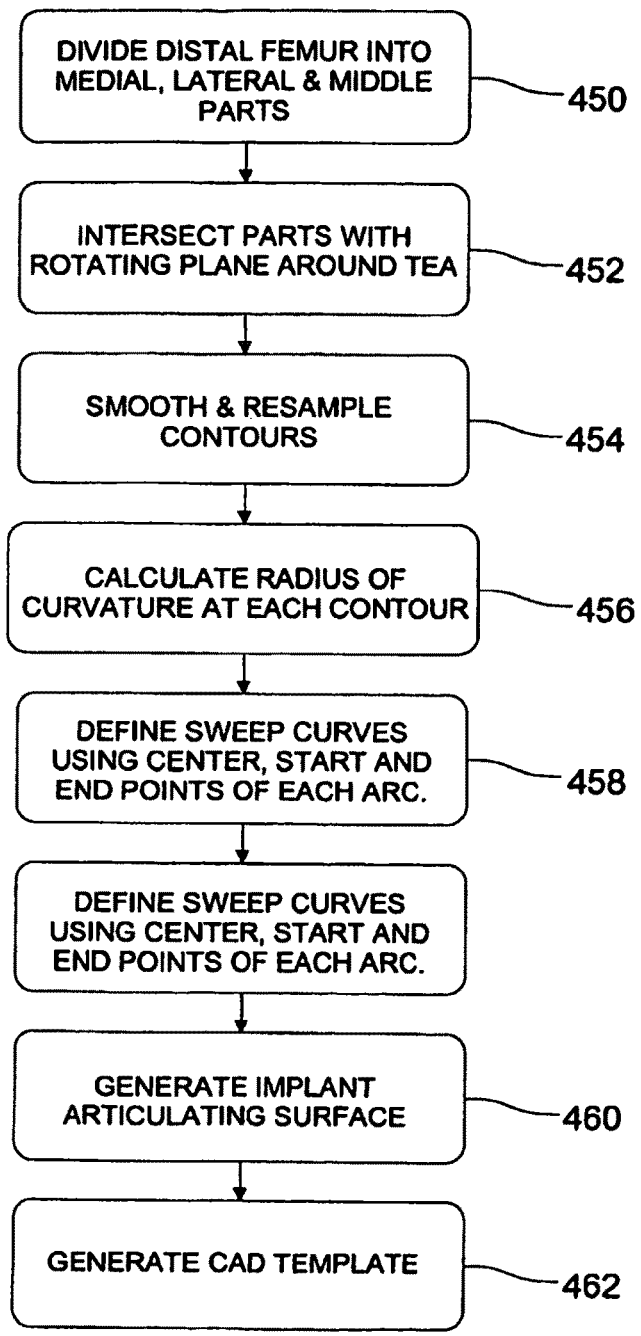
FIG. 16 is a flowchart describing an exemplary process of articulate surface mapping.
Figure 17:
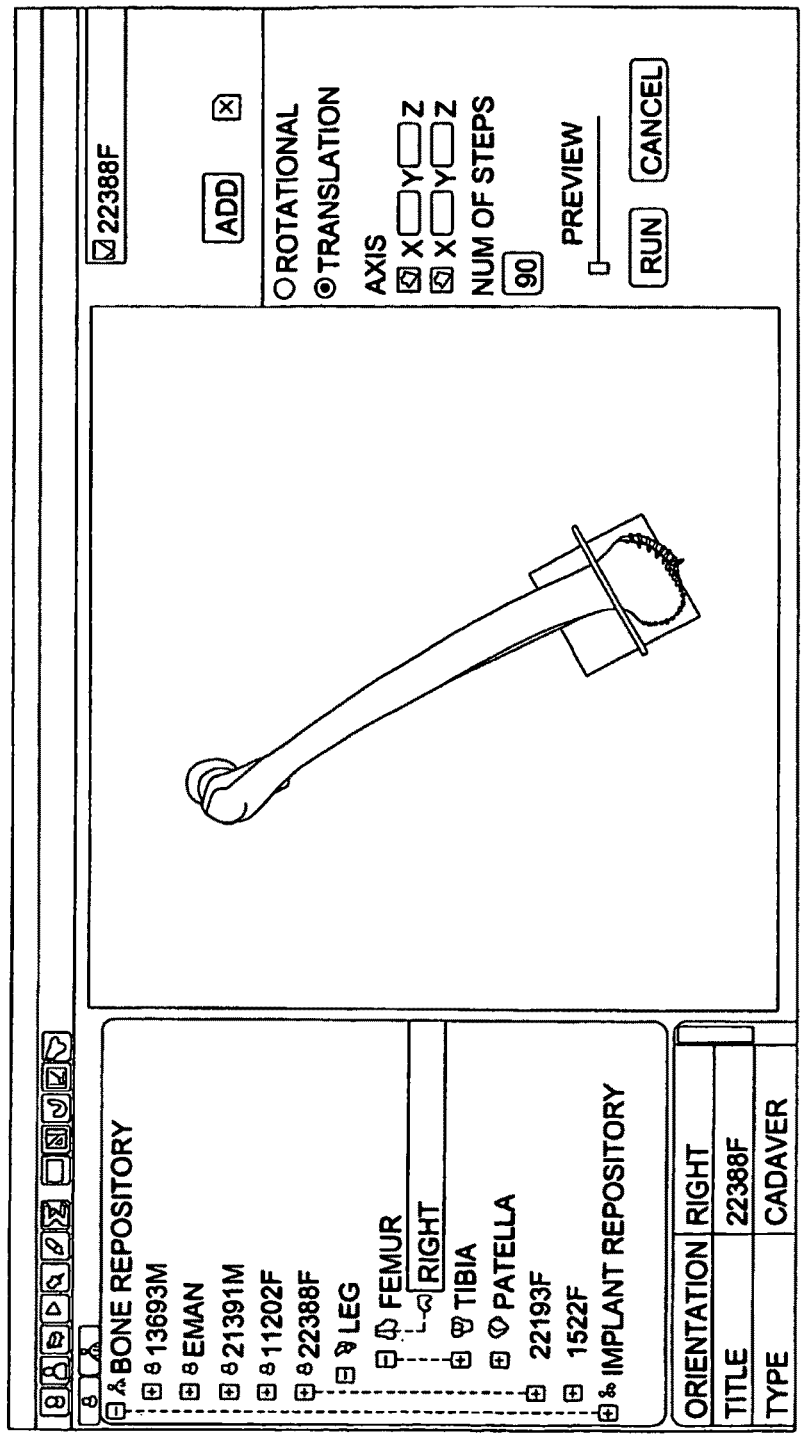
FIG. 17 and FIG. 18 are screenshots showing an exemplary contour analysis editor.
Figure 18:
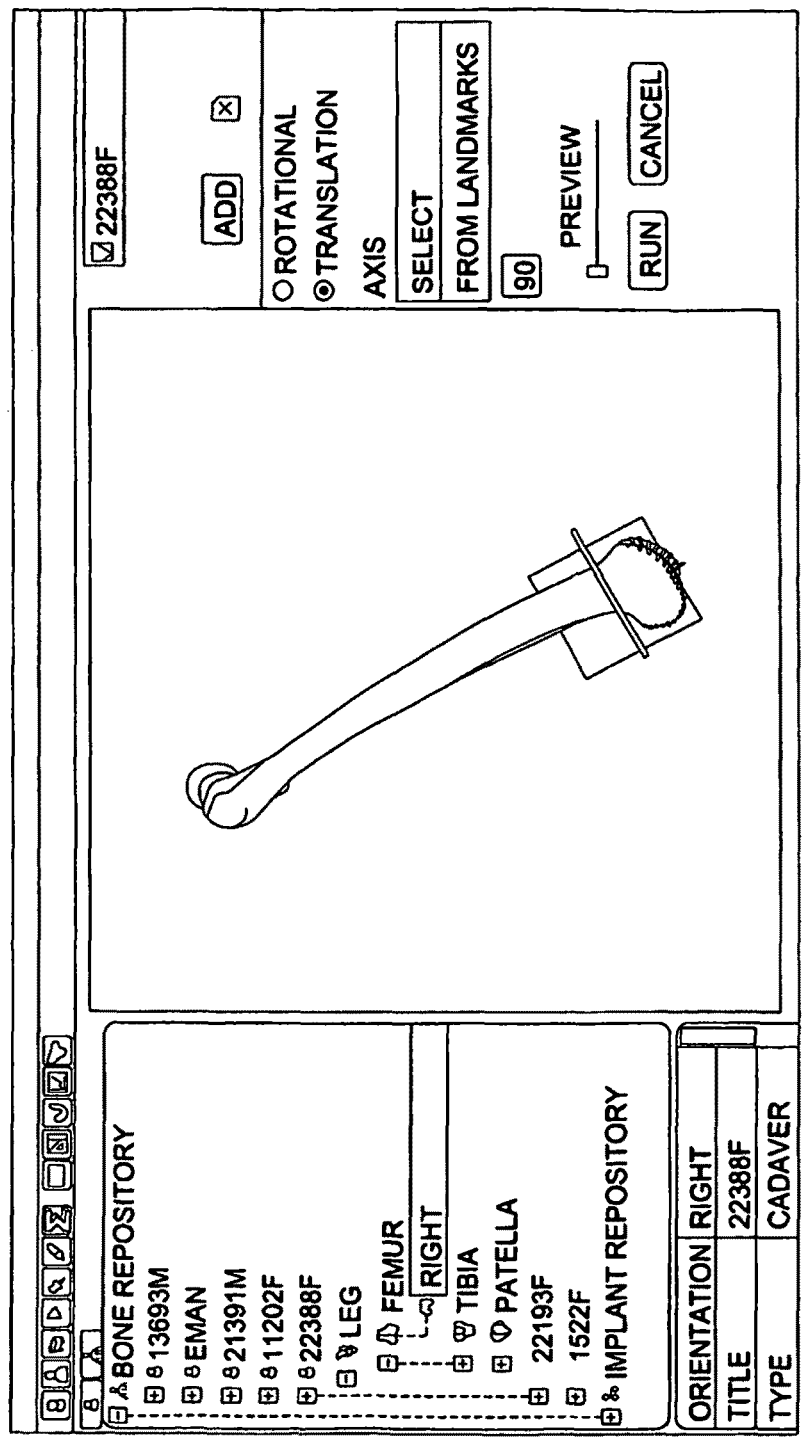

In an exemplary embodiment, once the cutting box has been produced, articular surface mapping may be performed. FIG. 16 is a detailed flowchart of an exemplary process for mapping an articular surface of a femur to generate an implant surface. The exemplary process begins by dividing the distal femora into three regions 450: lateral, medial and middle. Each of these regions is then intersected 452 with a set of planes rotating around the transepicondylar axis and with a 10 degree increment. FIG. 14 is a screenshot showing exemplary articular surface mapping and FIG. 15 is a screenshot showing an exemplary translation of an articulate surface into an implant design. Output contours are then smoothed and resampled 454. Radii of curvature of output curves are then calculated 456 by fitting a circle in each of these contours. Sweep curves are then defined 458 using the highest points on each of the medial and lateral curves. The sweep curves are then used to generate 460 a solid surface for the articular surface. Once the articular surface has been generated, a CAD template can be generated 462.

Figure 24:
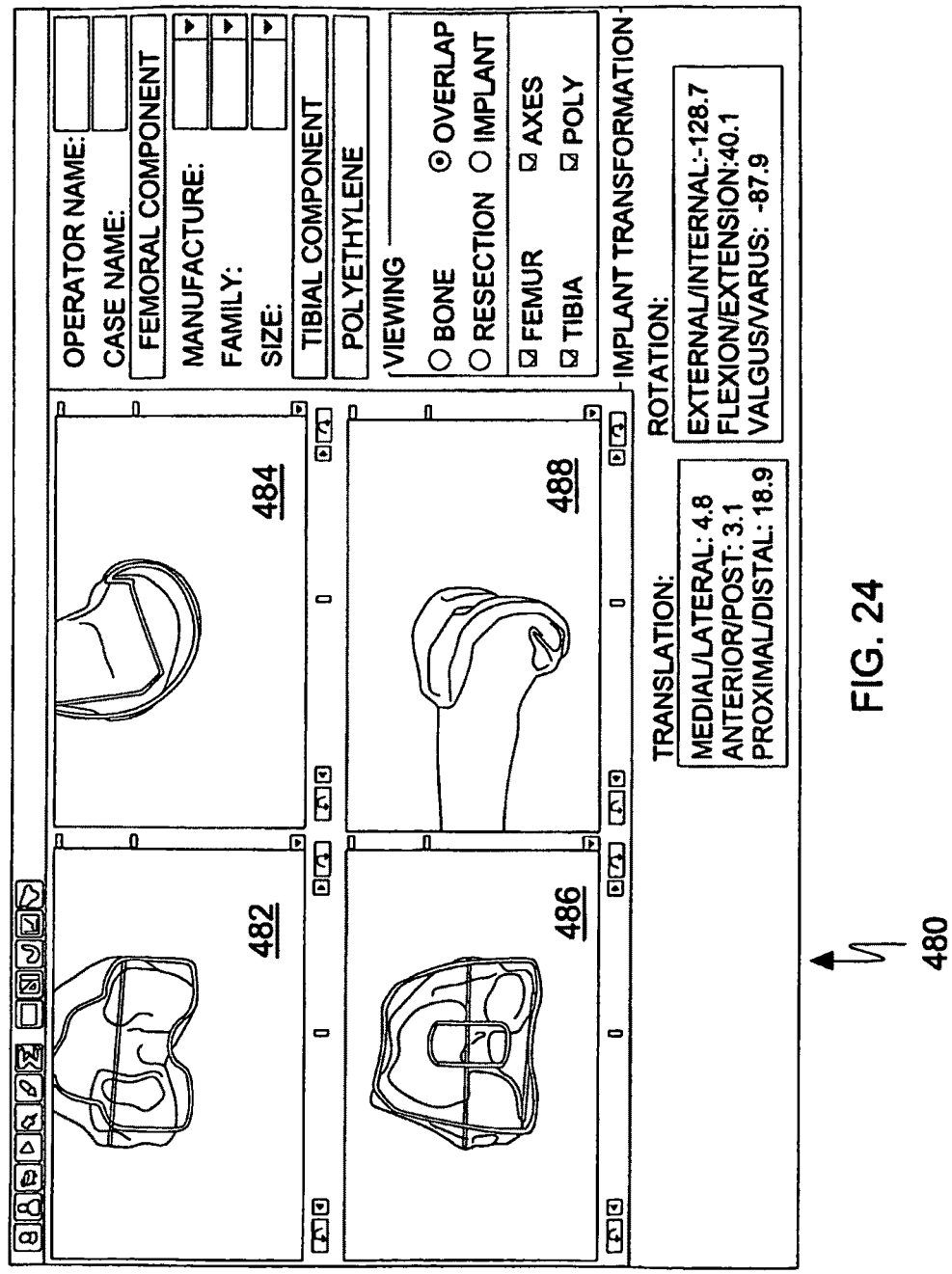
FIG. 24 screenshot showing virtual resection tool and component placement and evaluation.

In an exemplary embodiment, once the cutting box and articular surface have been produced, the implant fitting on a given bone can begin. An automatic implant fitting feature may accommodate different surgical placement techniques; however, the implant can also be manually manipulated in 3D or 2D orthogonal views. FIG. 24 shows exemplary virtual templating software 480 which may be used to evaluate an implant, with three orthogonal views 482, 484, 486 and one three dimensional view 488. In exemplary embodiments, the amount of bone resected can be evaluated along with the placement of the implant. After placement is complete, a contour of the bone after resection may be created and analyzed. These contours are then flattened, similar to a footprint.

Figure 25:
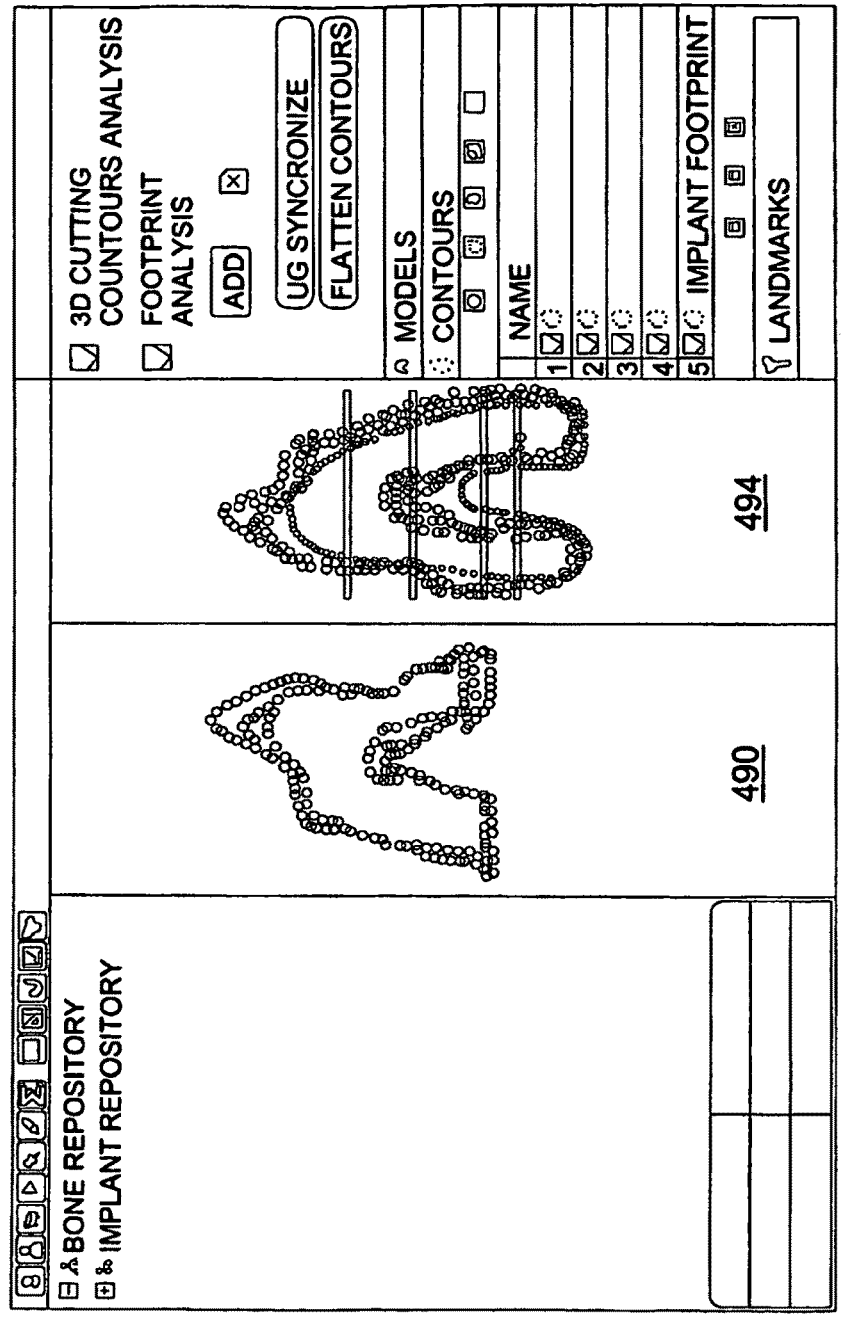
FIG. 25 is a screenshot showing an exemplary 3D contour analysis and implant footprint analysis.

In the exemplary embodiments, each bone from the database that was fitted with the implant may have a specific footprint contour associated with it. Two comparisons of implant fitting can be performed. The first comparison is to the existing bones in the database. The contours from each of the footprints, including the implant, are flattened and stacked upon one another for visualization. The shape of the implant may be automatically morphed to better fit the mean in the population of bones or the user can manually measure the data and alter the design. FIG. 25 is a screenshot showing an exemplary 3D contour analysis 490 and implant footprint analysis 494.

Figure 26:
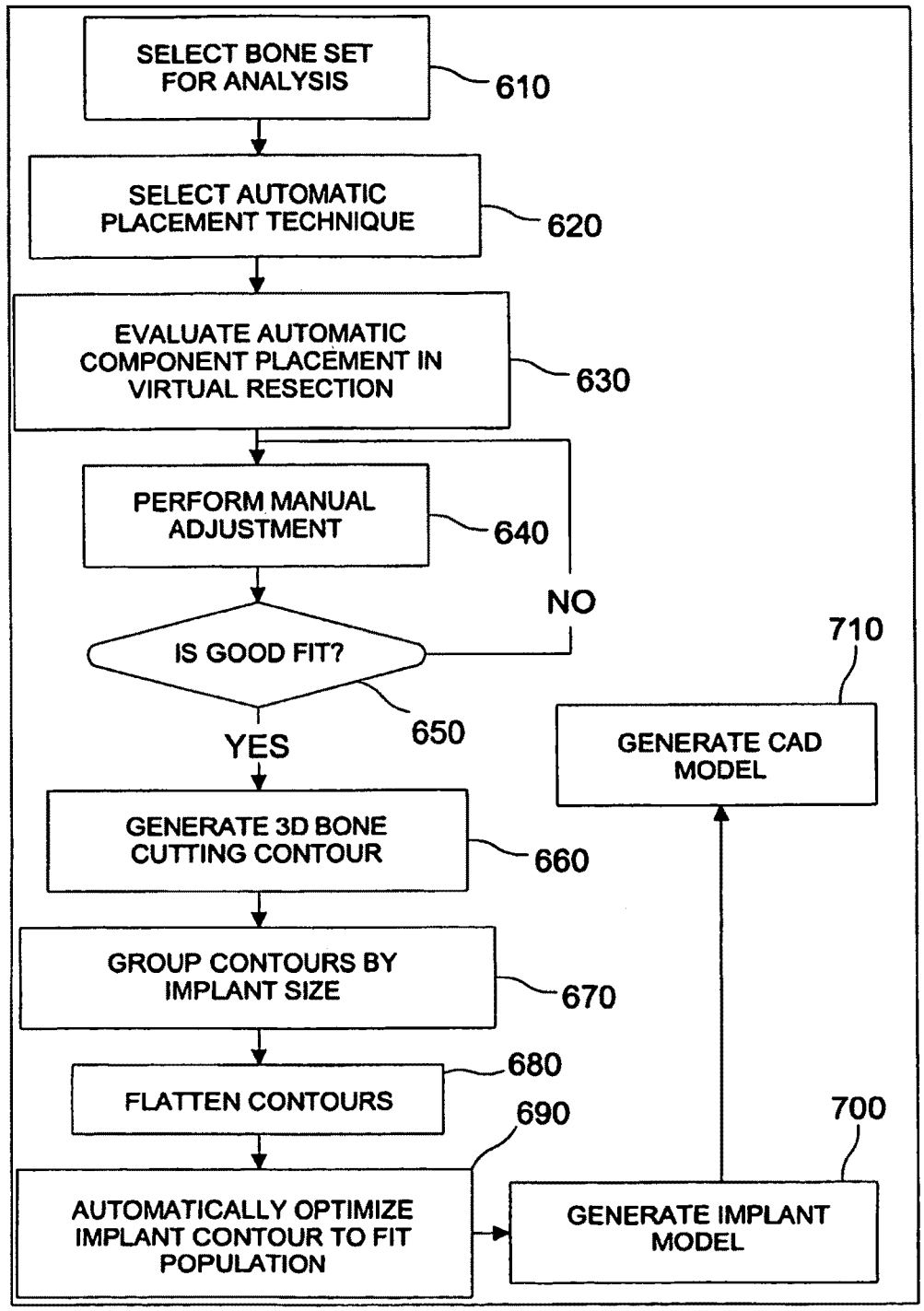
FIG. 26 is a flowchart describing an exemplary process of modifying implant shape and contour to fit population anatomy.

In exemplary embodiments, the second type of comparison is to other implants on the market. An assortment of implants may be stored in a database. Multiple implants from different manufacturers may be included and new implants can be added at any time. A footprint is generated for each of the implants in the database. These contours are grouped by size and stacked upon one another to evaluate the placement of the newly generated or modified implant to those currently being sold on the market. Implants from the same manufacturer, implant family, or size, for example, can be clustered together for specific comparisons as well. Again, data from the Implant Repository can be outputted for use in CAD software, such as Unigraphics. FIG. 26 is a flowchart describing an exemplary process of modifying implant shape and contour to fit population anatomy. In this example, the process begins with selecting a bone set for analysis 610. Then, the user selects an automatic placement technique 620. The user then evaluates the automatic component placement using virtual resection 630. The user may perform any necessary manual adjustment 640, after which the user determines whether the fit is good 650. If not, the manual adjustment 640 is repeated. If the fit is good, a 3D bone cutting contour is generated 660. The contours are then grouped by implant size 670 and the contours are flattened 680. The implant contours are automatically optimized to fit the population 690. Finally, an implant model is generated 700 and a CAD model is generated 710.

In the exemplary embodiments, virtual resection provides the ability to perform implant sizing, placement, and visualization on selected bone sets. Users may select particular implants and implant families on which to perform these functions. Users may select from predefined or user-defined surgical techniques for placing the implant components and users may define new surgical techniques for placement of both femoral and tibial components, for example, based on landmarks and axes. Users may visualize resections, full intact bones, and/or implants placed on resected bones, for example. In an exemplary embodiment, users may be provided with three 2D orthogonal views and one 3D view for visualization and implant manipulation. Users may modify implant size, family, and manufacturer information. Visualizations may include axes and landmarks overlaid on bones. Fitting results may be saved to the smart database. A surgeon may utilize the various capabilities described herein to perform virtual templating, implant placement, virtual resection, and implant manipulation, thereby producing quantitative results.

In exemplary embodiments, an implant editor interface provides the ability to import CAD models (such as Unigraphics, Autodesk ProE, etc.) of various implants into an implant database. Users may view and visualize 3D models of implants or 2D implant footprints of implants within the database. Exemplary implant editors allow geometrical measurements of implants and statistical analysis of the results. Further, users may correlate implant design parameters with 3D models of implants and may view and modify implant design parameters. Exemplary embodiments provide the capability to export design parameters to CAD software (such as Unigraphics, Autodesk ProE, etc.) to update CAD models.

Figure 19:
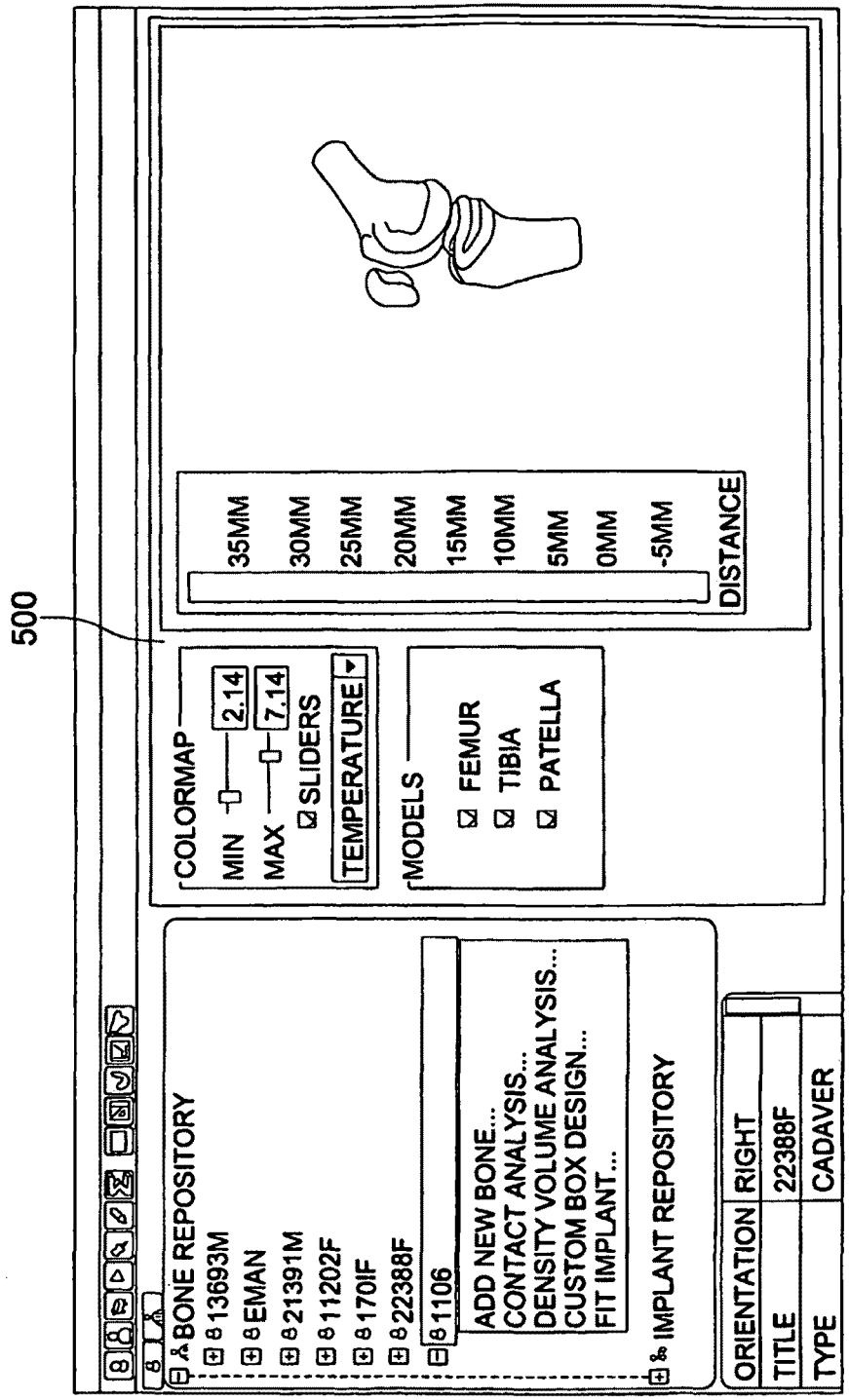
FIG. 19 is a screenshot showing an exemplary kinematics and contact analysis editor.

An exemplary Kinematic Editor examines the kinematics of both normal and implanted joints. FIG. 19 is a screenshot showing an exemplary kinematics and contact analysis editor 500. Normal knee joint movement can be evaluated for patellar tracking, for example. The range of motion for implanted knee joints is beneficial when simulating how the implant will perform. Potential problems may be identified during this step if implant overlap or movement is observed. In this exemplary embodiment, ACL (anterior cruciate ligament) deficient knees may be included in a separate category. The average motions of knee joints were tracked through past studies that utilized fluoroscopy and implants. In addition, contact mapping of the joint reveals areas with the highest and lowest points of contact.

Figure 23:
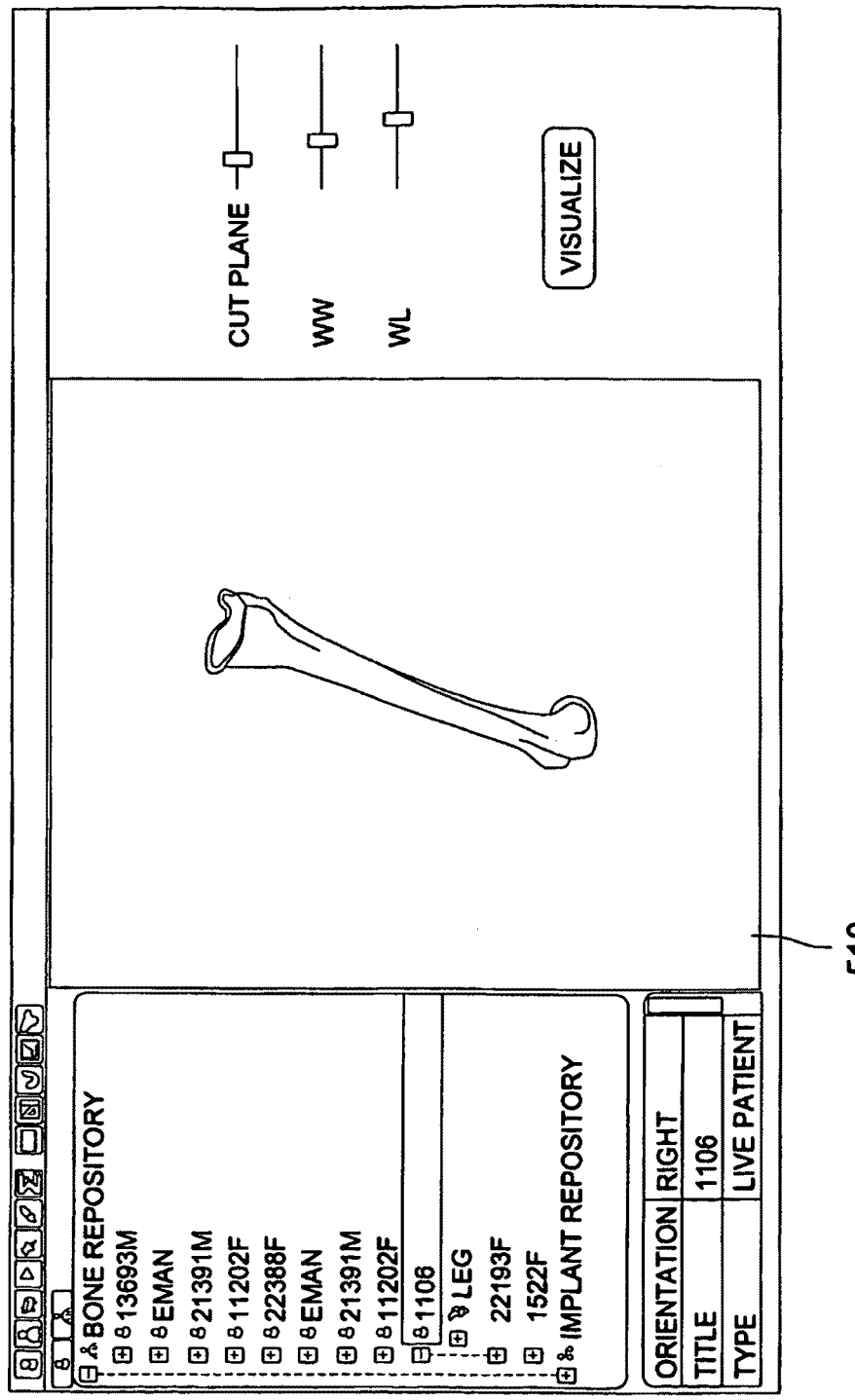
FIG. 23 is a screenshot showing an exemplary 3D density map superimposed with an exemplary surface model.

In the exemplary embodiments, finite element analysis (FEA) can be performed on the bone-implant interface to simulate stress distribution, for example. A density map for each bone in the database may be created using a tissue mimicking phantom and CT data. This information is stored within the database in the form of meshes associated with the density. Differences between the cortical and trabecular bone can be viewed within the 3D model, which also illustrates the surface generated from the CT data. FIG. 23 is a screenshot showing an exemplary 3D density map 510 superimposed with an exemplary surface model.

In the exemplary embodiments, a script editor may provide scripting functions, including defining landmarks, axes, measurements, and contours as well as performing mathematical and statistical operations. In addition, the script editor may allow landmark detection, axes detection, measurements, and/or contours on selected bone sets. Further, it may allow running of mathematical or statistical operations on saved or generated measurements. Exemplary script editors may allow definition of geometrical elements (such as surfaces, vectors, planes, circles, spheres, etc.) based on landmarks or axes. Saved surface patches may be utilized as localized search areas for landmark detections.

While exemplary embodiments of the invention have been set forth above for the purpose of disclosure, modifications of the disclosed embodiments of the invention as well as other embodiments thereof may occur to those skilled in the art. Accordingly, it is to be understood that the invention is not limited to the above precise embodiments and that changes may be made without departing from the scope of the invention. Likewise, it is to be understood that it is not necessary to meet any or all of the stated advantages or objects of the invention disclosed herein to fall within the scope of the invention, since inherent and/or unforeseen advantages of the present invention may exist even though they may not have been explicitly discussed herein. All references mentioned herein are incorporated by reference.

What is claimed is:

1. A method of designing a prosthetic implant, comprising the steps of:
    (a) obtaining three dimensional data corresponding to an existing or prototype orthopaedic implant or component thereof;
    (b) obtaining three dimensional data corresponding to a same type of bone to provide a population of bone data comprising multiple bones;
    (c) associating at least one of the multiple bones from the population with the three dimensional data corresponding to the existing or prototype orthopaedic implant or component thereof to establish a first virtual replacement having a first configuration;
    (d) taking the first virtual replacement through a simulated range of movement and recording data;
    (e) associating at least another one of the multiple bones from the population with the three dimensional data corresponding to the existing or prototype orthopaedic implant or component thereof to establish a second virtual replacement having a first configuration;
    (f) taking the second virtual replacement through a simulated range of movement and recording data; and
    (g) comparing the recorded data from the first virtual replacement range of motion to the second virtual replacement range of motion to qualitatively evaluate the an existing or prototype orthopaedic implant or component thereof.

2. A method of designing a prosthetic implant, comprising the steps of:
    (a) obtaining three dimensional data corresponding to a first existing or prototype orthopaedic implant or component thereof;
    (b) obtaining three dimensional data corresponding to a same type of bone to provide a population of bone data comprising multiple bones;
    (c) associating at least one of the multiple bones from the population with the three dimensional data corresponding to the first existing or prototype orthopaedic implant or component thereof to establish a first virtual replacement having a first configuration;
    (d) taking the first virtual replacement through a simulated range of movement and recording data;
    (e) obtaining three dimensional data corresponding to a second existing or prototype orthopaedic implant or component thereof;
    (f) associating at least one of the multiple bones from the population with the three dimensional data corresponding to the second existing or prototype orthopaedic implant or component thereof to establish a second virtual replacement having a first configuration;
    (g) taking the second virtual replacement through a simulated range of movement and recording data;
    (h) comparing the recorded data from the first virtual replacement range of motion to the second virtual replacement range of motion to qualitatively evaluate the first and second existing or prototype orthopaedic implants or components thereof.

3. A method of designing an orthopaedic implant, comprising the steps of:
    (a) obtaining three dimensional data corresponding to an existing or prototype orthopaedic implant or component thereof;
    (b) obtaining three dimensional data corresponding to a same type of bone to provide a population of bone data comprising multiple bones, where each of the multiple bones mimics a bone resurfaced to receive the existing or prototype orthopaedic implant or component thereof;
    (c) associating, separately, at least two of the multiple bones from the population with the three dimensional data corresponding to the existing or prototype orthopaedic implant or component thereof to establish a virtual replacement;
    (d) taking the virtual replacement through a simulated range of movement and recording data to generate statistics throughout the range of movement; and
    (e) responsive to the statistics, modifying the existing or prototype orthopaedic implant or component thereof.

4. The method of claim 3, wherein the three dimensional data corresponding to an existing or prototype orthopaedic implant or component thereof is generated by a three dimensional scan orthopaedic implant or component thereof.

5. The method of claim 3, wherein the three dimensional data corresponding to an existing or prototype orthopaedic implant or component thereof is generated by a CAD model of the orthopaedic implant or component thereof.

6. The method of claim 3, wherein the three dimensional data corresponding to the population of bone data is generated at least in part by a three dimensional scan of at least one bone of the multiple bones.

7. The method of claim 3, wherein the three dimensional data corresponding to the population of bone data is generated at least in part from a compilation of two dimensional scans of at least one bone of the multiple bones.

8. The method of claim 3, wherein the three dimensional data corresponding to the population of bone data is generated at least in part from artificial data.

9. The method of claim 3, further comprising the step of associating at least one of a landmark and an axis with each of the multiple bones of the population.

10. The method of claim 9, wherein mimicking the resurfacing of bone across the population occurs subsequent to the step of associating at least one of the landmark and the axis with each of the multiple bones of the population.

11. The method of claim 3, wherein the recorded data includes at least one of contact area of the existing or prototype orthopaedic implant or component thereof.

12. The method of claim 3, wherein the recorded data includes at least one of bone rotation and bone angle.

* * * * *